United States Patent
Azarin et al.

(10) Patent No.: US 11,980,410 B2
(45) Date of Patent: May 14, 2024

(54) COMPOSITE SCAFFOLDS FOR THERMAL ABLATION OF METASTATIC CANCER CELLS

(71) Applicant: Regents of the University of Minnesota, Minneapolis, MN (US)

(72) Inventors: Samira M. Azarin, Woodbury, MN (US); Francisco Pelaez, Minneapolis, MN (US); Navid Manuchehrabadi, Marlborough, MA (US); John C. Bischof, Saint Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1328 days.

(21) Appl. No.: 16/152,769

(22) Filed: Oct. 5, 2018

(65) Prior Publication Data
US 2019/0105094 A1   Apr. 11, 2019

Related U.S. Application Data

(60) Provisional application No. 62/568,644, filed on Oct. 5, 2017.

(51) Int. Cl.
*A61B 18/08* (2006.01)
*A61F 7/00* (2006.01)
(Continued)

(52) U.S. Cl.
CPC ............... *A61B 18/08* (2013.01); *A61F 7/00* (2013.01); *A61L 31/022* (2013.01); *A61L 31/10* (2013.01); *A61L 31/14* (2013.01); *A61L 31/146* (2013.01); *A61B 2018/00065* (2013.01); *A61B 2018/00077* (2013.01); *A61B 2018/00113* (2013.01); *A61B 2018/00136* (2013.01);
(Continued)

(58) Field of Classification Search
CPC ... A61B 18/08; A61F 2/06; A61F 2/82; A61K 49/00; G08C 19/16; A61L 27/44; A61L 33/06
See application file for complete search history.

(56) References Cited

U.S. PATENT DOCUMENTS 6,312,463 B1 * 11/2001 Rourke ............... A61F 2/91
                                                  623/1.2
6,939,477 B2    9/2005 Stark et al.
(Continued)

FOREIGN PATENT DOCUMENTS

WO    WO/2016/161148    * 10/2016 ............. A61L 27/44

OTHER PUBLICATIONS

Aravalli et al., "Spectroscopic and Calorimetric Evaluation of Chemically Induced Protein Denaturation in HuH-7 Liver Cancer Cells and Impact on Cell Survival," Technology in Cancer Research & Treatment, vol. 11, No. 5, Oct. 2012, 7 pp.
(Continued)

*Primary Examiner* — Dah-Wei D. Yuan
*Assistant Examiner* — Andrew J Bowman
(74) *Attorney, Agent, or Firm* — Shumaker & Sieffert, P.A.

(57) ABSTRACT

A device includes an electrically conductive or electrically semiconductive material and a biocompatible porous scaffold around the electrically conductive or electrically semiconductive material. The biocompatible porous scaffold includes a biocompatible polymer and pores configured to capture metastatic cells.

14 Claims, 14 Drawing Sheets

(51) Int. Cl.
*A61L 31/02* (2006.01)
*A61L 31/10* (2006.01)
*A61L 31/14* (2006.01)
*A61B 18/00* (2006.01)

(52) U.S. Cl.
CPC ............... *A61B 2018/00577* (2013.01); *A61B 2018/087* (2013.01); *A61F 2007/009* (2013.01); *A61L 2400/08* (2013.01); *A61L 2400/18* (2013.01)

(56) References Cited

U.S. PATENT DOCUMENTS

| | | | | |
|---|---|---|---|---|
| 2008/0109072 | A1* | 5/2008 | Girton | A61L 31/148 623/1.49 |
| 2009/0041845 | A1* | 2/2009 | Kleiner | A61L 31/16 424/484 |
| 2010/0312331 | A1* | 12/2010 | Pickett | A61L 33/06 526/263 |
| 2014/0072510 | A1* | 3/2014 | Shea | A61K 49/0004 424/9.1 |
| 2017/0281798 | A1 | 10/2017 | Shea et al. | |
| 2019/0008971 | A1 | 1/2019 | Shea et al. | |

OTHER PUBLICATIONS

Asparuhova et al., "Mechanism of Irradiation-induced Mammary Cancer Metastasis: A Role for SAP-Dependent Mkl1 Signaling," Molecular Oncology, vol. 9, No. 8, Oct. 2015, 18 pp.
Atkinson et al., "Usable Frequencies in Hyperthermia with Thermal Seeds," IEEE Transactions on Biomedical Engineering, vol. BME-31, Issue 1, Jan. 1984, 6 pp.
Azarin et al., "In vivo Capture and Label-Free Detection of Early Metastatic Cells," Nature Communications, No. 6, Sep. 2015, 9 pp.
Barth, "Infrared Spectroscopy of Proteins," Biochimica at Biophysica Acta, vol. 1767, No. 9, Sep. 2007, 29 pp.
Bersani et al., "Bioengineered Implantable Scaffolds as a Tool to Study Stromal-Derived Factors in Metastatic Cancer Models," Cancer Research, vol. 74, Dec. 2014, 11 pp.
Bertrand et al., "Biocompatibility Aspects of New Stent Technology," Journal of the American College of Cardiology, vol. 32, No. 3, Sep. 1998, 10 pp.
Buckley et al., "Inductively Heated Shape Memory Polymer for the Magnetic Actuation of Medical Devices," IEEE Transactions on Biomedical Engineering, vol. 53, No. 10, Oct. 2006, 9 pp.
Chu et al., "Thermal Ablation of Tumours: Biological Mechanisms and Advances in Therapy," Nature Reviews Cancer, vol. 14, Mar. 2014, 10 pp.
De Scheerder et al., "Biocompatibility of Biodegradable and Nonbiodegradable Polymer-Coated Stents Implanted in Porcine Peripheral Arteries," CardioVascular and Interventional Radiology, vol. 18, No. 4, Jul. 1995, 6 pp.
Diederich, "Thermal Ablation and High-Temperature Thermal Therapy: Overview of Technology and Clinical Implementation," International Journal of Hyperthermia, vol. 21, No. 8, Dec. 2005, 9 pp.
Etheridge et al., "Optimizing Magnetic Nanoparticle based Thermal Therapies Within the Physical Limits of Heating," Annals of Biomedical Engineering, vol. 41, No. 1, Jan. 2013, 11 pp.
Gautam et al., "Practical Considerations for Maximizing Heat Production in a Novel Thermobrachytherapy Seed Prototype," Medical Physics, vol. 41, No. 2, Feb. 2014, 10 pp.
Gloria, et al., "Magnetic Poly($\epsilon$-caprolactone)/Iron-Doped Hydroxyapatite Nanocomposite Substrates for Advanced Bone Tissue Engineering," Journal of the Royal Society Interface, vol. 10, No. 80, Mar. 2013, 11 pp.
Gottesman, "Mechanisms of Cancer Drug Resistance," Annual Review of Medicine, vol. 53, Feb. 2002, 15 pp.
Gundem et al., "The Evolutionary History of Lethal Metastatic Prostate Cancer," Nature, vol. 520, Apr. 2015, 24 pp.

He et al., "In Situ Thermal Denaturation of Proteins in Dunning AT-1 Prostate Cancer Cells: Implication for Hyperthermic Cell Injury," Annals of Biomedical Engineering, vol. 32, No. 10, Oct. 2004, 15 pp.
He et al., "Thermal Therapy in Urologic Systems: A Comparison of Arrhenius and Thermal Isoeffective Dose Models in Predicting Hyperthermic Injury," Journal of Biomechanical Engineering, vol. 131, No. 7, Jul. 2009, 14 pp.
He et al., "Quantification of Temperature and Injury Response in Thermal therapy and Cryosurgery," Critical Reviews in Biomedical Engineering, vol. 31, Dec. 2003, 68 pp.
Hildebrandt et al., "The Cellular and Molecular basis of Hyperthermia," Critical Reviews in Oncology/Hematology, vol. 43, Jul. 2002, 24 pp.
Hlavaty et al., "Enhancing Human Islet Transplantation by Localized Release of Trophic Factors from PLG Scaffolds," American Journal of Transplantation, vol. 14, No. 7, Jul. 2014, 10 pp.
Jang et al., "Plasmid Delivery in Vivo from Porous Tissue-Engineering Scaffolds: Transgene Expression and Cellular Transfection," Molecular Therapy, vol. 12, No. 3, Sep. 2005, 9 pp.
Jiang et al., "Pre-Conditioning Cryosurgery: Cellular and Molecular Mechanisms and Dynamics of TNF-$\alpha$ Enhanced Cryotherapy in In Vivo Prostate Cancer Model System," Cryobiology, vol. 61, No. 3, Dec. 2010, 19 pp.
Johannsen et al., "Magnetic Nanoparticle Hyperthermia for Prostate Cancer," International Journal of Hyperthermia, vol. 26, Dec. 2010, 6 pp.
Kaplan et al., "Preparing the "Soil": The Premetastatic Niche", Cancer Research, vol. 66, No. 23, Dec. 2006, 6 pp.
Kaplan et al., "VEGFR1-positive Haematopoietic Bone Marrow Progenitors Initiate the Pre-Metastatic Niche," Nature, vol. 438, Dec. 2005, 19 pp.
Kim et al., "Magnetic Scaffolds of Polycaprolactone with Functionalized Magnetite Nanoparticles: Physicochemical, Mechanical, and Biological Properties Effective for Bone Regeneration," RSC Advances, vol. 4, No. 33, Mar. 2014, 36 pp.
Kim et al., "Tumor Self-Seeding by Circulating Cancer Cells," Cell, vol. 139, No. 7, Dec. 2009, 12 pp.
Ko et al., "The Use of Chemokine-Releasing Tissue Engineering Scaffolds in a Model of Inflammatory Response-Mediated Melanoma Cancer Metastasis," Biomaterials, vol. 33, Jan. 2012, 20 pp.
Kong et al., "Fourier Transform Infrared Spectroscopic Analysis of Protein Secondary Structures," Acta Biochimica at Biophysica Sinica, vol. 39, No. 8, Aug. 2007, 11 pp.
Kregel, "Molecular Biology of Thermoregulation Invited Review: Heat Shock Proteins: Modifying Factors in Physiological Stress Responses and Acquired Thermotolerance," Journal of Applied Physiology, vol. 95, May 2002, 10 pp.
Labet et al., "Synthesis of Polycaprolactone: A Review," Chemical Society Reviews, vol. 38, No. 12, Jan. 2009, 21 pp.
Lepock, "Cellular Effects of Hyperthermia: Relevance to the Minimum Dose for Thermal Damage," International Journal of Hyperthermia, vol. 19, No. 3, May 2003, 15 pp.
Lepock et al., "Protein Denaturation in Intact Hepatocytes and Isolated Cellular Organelles during Heat Shock," The Journal of Cell Biology, vol. 122, No. 6, Sep. 1993, 10 pp.
Li et al., Natural Killer Cells-Produced IFN-Improves Bone Marrow-Derived Hepatocytes Regeneration in Murine Liver Failure Model, Scientific Reports, 5, Article No. 13687, Sep. 2015, 11 pp.
Ma et al., "3D Printing of Biomaterials with Mussel-Inspired Nanostructures for Tumor therapy and tissue Regeneration," Biomaterials, vol. 111, Dec. 2016, 11 pp.
Mandracci et al., "Surface Treatments and Functional Coatings for Biocompatibility Improvement and Bacterial Adhesion Reduction in Dental Implantology," Coatings, vol. 6, No. 1, Jan. 2016, 22 pp.
Mansour et al., "Materials for Pharmaceutical Dosage Forms: Molecular Pharmaceutics and Controlled Release Drug Delivery Aspects," International Journal of Molecular Sciences, vol. 11, No. 9, Sep. 2010, 25 pp.
Manuchehrabadi et al., "Improved Tissue Cryopreservation Using Inductive Heating of Magnetic Nanoparticles," Science Translational Medicine, vol. 9 No. 379, Mar. 2017, 11 pp.

(56) References Cited

OTHER PUBLICATIONS

Natesan et al., "A Micro-Thermal Sensor for Focal Therapy Applications," Scientific Reports, vol. 6, Feb. 2016, 8 pp.

Nguyen et al., "Metastasis: From Dissemination to Organ-Specific Colonization," Nature Reviews Cancer, vol. 9, No. 4, Apr. 2009, 12 pp.

Pelaez et al., "Biomaterial Scaffolds for Non-Invasive Focal Hyperthermia as a Potential Tool to Ablate Metastatic Cancer Cells," Biomaterials, vol. 166, Jun. 2018, 17 pp.

Pennes, "Analysis of Tissue and Arterial Blood Temperatures in the Resting Human Forearm," Journal of Applied Physiology, vol. 1, No. 2, Aug. 1948, 30 pp.

Qin et al., "Correlated Parameter Fit of Arrhenius Model for Thermal Denaturation of Proteins and Cells," Annals of Biomedical Engineering, vol. 42, No. 12, Dec. 2014, 25 pp.

Rao et al., "Enhanced Survival with Implantable Scaffolds That Capture Metastatic Breast Cancer Cells In Vivo," Cancer Research, vol. 76, No. 18, Sep. 2016, 10 pp.

Sapareto et al., "Effects of Hyperthermia on Survival and Progression of Chinese Hamster Ovary Cells," Cancer Research, vol. 38, Feb. 1978, 9 pp.

Savitzky et al., "Smoothing and Differentiation of Data by Simplified Least Squares Procedures," Analytical Chemistry, vol. 36, No. 8, Jul. 1964, 13 pp.

Shastri, "Non-Degradable Biocompatible Polymers in Medicine: Past, Present and Future," Current Pharmaceutical Biotechnology, vol. 4, No. 5, Oct. 2003, 8 pp.

Sorensen et al., "Quantification of B16 Melanoma Cells in Lungs Using Triplex Q-PCR—A New Approach to Evaluate Melanoma Cell Metastasis and Tumor Control," PloS One, vol. 9, No. 1, Jan. 2014, 9 pp.

Stauffer et al., "Magnetic Induction Heating of Ferromagnetic Implants for Inducing Localized Hyperthermia in Deep-Seated Tumors," IEEE Transactions on Biomedical Engineering, vol. BME-31, No. 2, Feb. 1984, 17 pp.

Subia et al., "Biomaterial Scaffold Fabrication Techniques for Potential Tissue Engineering Applications," Tissue Engineering, Mar. 2010, 19 pp.

Svaasand, "Photodynamic and Photohyperthermic Response of Malignant Tumors," Medical Physics, vol. 12, No. 4, Jul. 1985, 9 pp.

Thomsen, "Nonthermal Effects in Thermal Treatment Applications of Nonionizing Irradiation," Proceedings vol. 5698 Thermal Treatment of Tissue: Energy Delivery and Assessment III, Proceedings of SPIE, Apr. 2005, 15 pp.

Van der Zee, "Heating the Patient: A Promising Approach?" Annals of Oncology, vol. 13, Aug. 2002, 12 pp.

Wolkers et al., "Effects of Freezing on Membranes and Proteins in LNcAP Prostate Tumor Cells," Biochimica et Biophysica Acta, vol. 1768, No. 3, Mar. 2007, 9 pp.

Wolkers et al., "In Situ FTIR Studies on Mammalian Cells," Spectroscopy, vol. 24, No. 5, Jan. 2010, 11 pp.

Xu et al., "Characteristics and Cytocompatibility of Biodegradable Polymer Film on Magnesium by Spin Coating," Colloids and Surfaces B: Biointerfaces, vol. 93, May 2012, 8 pp.

Zhang et al., "3D-printed Magnetic Fe304/MBG/PCL Composite Scaffolds with Multifunctionality of Bone Regeneration, Local Anticancer Drug Delivery and Hyperthermia," Journal of Materials Chemistry B, vol. 2, No. 43, Sep. 2014, 13 pp.

Zhang et al., "Composite Scaffolds of Gelatin and Gold Nanoparticles with Tunable Size and Shape for Photothermal Cancer Therapy," Journal of Materials Chemistry B, vol. 5, No. 2, Jan. 2017, 9 pp.

\* cited by examiner

COMPOSITE SCAFFOLDS FOR THERMAL ABLATION OF METASTATIC CANCER CELLS

This application claims the benefit of U.S. Provisional Application No. 62/568,644, filed Oct. 5, 2017, the entire content of which is incorporated by reference herein.

TECHNICAL FIELD

The disclosure relates to devices for treating cancer.

BACKGROUND

Many cancer deaths result from metastatic spread of the primary tumor to vital organs. Currently, there are few therapeutic options for treatment of metastatic disease, as it often remains undetected until the burden of disease is too high. Disseminated tumor cells are not bound to remain in one location, as both re-seeding of the primary tumor site and direct spreading from one metastatic site to another may occur.

SUMMARY

In some examples, the disclosure describes a device that includes an electrically conductive or electrically semiconductive material and a biocompatible porous scaffold around the electrically conductive or electrically semiconductive material. The biocompatible porous scaffold includes a biocompatible polymer and pores configured to capture metastatic cells.

In some examples, the disclosure describes a method that includes forming a porous scaffold comprising a biocompatible polymer around an electrically conductive or electrically semiconductive material, wherein the porous scaffold defines pores configured to capture metastatic cancer cells.

In some examples, the disclosure describes a method that includes implanting a device in a body of a patient. The device includes an electrically conductive or electrically semiconductive material and a biocompatible porous scaffold around the electrically conductive or electrically semiconductive material. The biocompatible porous scaffold includes a biocompatible polymer and pores configured to capture metastatic cells. The method further includes applying an electromagnetic induction stimulus to the device at a target strength and target frequency for a target duration, wherein the electromagnetic induction stimulus is selected to cause the electrically conductive or electrically semiconductive material to heat at least a portion of the porous scaffold to at least a target temperature.

The details of one or more examples are set forth in the accompanying drawings and the description below. Other features, objects, and advantages of the disclosure will be apparent from the description and drawings, and from the claims.

DETAILED DESCRIPTION

The disclosure describes devices and techniques for capturing metastatic cells in vivo and treating the metastatic cells using non-invasive heating. An implant includes an electrically conductive or electrically semiconductive material and a biocompatible porous scaffold around the electrically conductive or electrically semiconductive material. The biocompatible porous scaffold comprises a biocompatible polymer and pores configured to capture metastatic cells. The electrically conductive or electrically semiconductive material may act as an inductively heated thermal source to heat the metastatic cells captured in the porous scaffold upon exposure to electromagnetic induction stimulus.

The implant maybe implanted in the body of a patient. Due to its biocompatibility, the implant may be left in the patient for a period of time. The pores of the biocompatible porous scaffold may recruit and capture metastatic cells migrating in the patient's body. Once a selected amount of metastatic cells have been captured by the implant, an electromagnetic induction stimulus, such as an oscillating magnetic field, may be applied to the implant. The electromagnetic induction stimulus may be an alternating magnetic field that induces current in the electrically conducting or electrically semiconducting material. The induced currents generate heat in the electrically conducting or electrically semiconducting material, which heats at least a portion of the porous scaffold to at least a target temperature, such as a temperature that kills the captured metastatic cancer cells. By indirectly inducing heat in the implant, the implant can kill the captured metastatic cancer cells without invasive attachment of a heat source. By capturing metastatic cells and destroying them, the implant describe above may improve treatment of metastatic disease.

Figure 1:
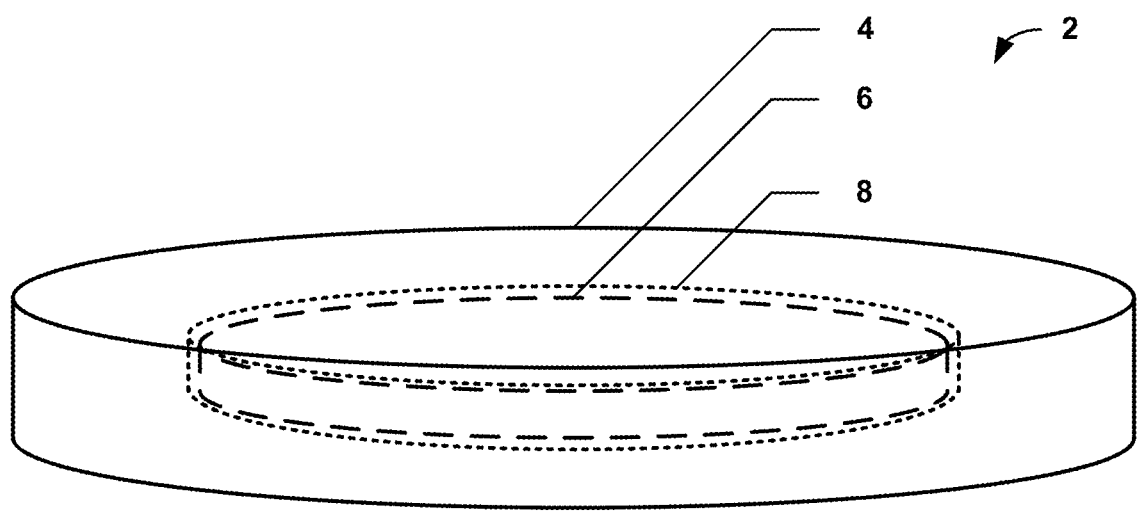
FIG. 1 is a conceptual and cross-sectional diagram illustrating an example implant for trapping and heating metastatic cells in tissue.

FIG. 1 is a conceptual and cross-sectional diagram illustrating an example implant 2 for trapping and heating metastatic cells in tissue. Implant 2 includes a biocompatible porous scaffold 4 around an electrically conductive or electrically semiconductive material 6. Implant 2 may optionally include a coating 8 between electrically conductive or electrically semiconductive material 6 and porous scaffold 4.

Porous scaffold 4 may be configured to capture metastatic cells. Porous scaffold 4 may support the entrapment, attachment, or growth of metastatic cells in pores or on surfaces of porous scaffold 4. By capturing metastatic cells, porous scaffold 4 may reduce or substantially prevent the spread of the metastatic cells to other tissues and contain the metastatic cells until and during heat application using electrically conductive or electrically semiconductive material 6.

Porous scaffold 4 includes pores configured to capture metastatic cells. Metastatic cells may be captured by a variety of mechanisms, such as entrapment, adhesion, absorption, or the like. In some examples, the pores may be sufficiently large to allow migration of cells into porous scaffold 4. In some examples, the pores have a size between about 100 µm and about 500 µm. In other examples, the pores may be configured to correspond in size to the size of the metastatic cells.

Porous scaffold 4 may include a variety of shapes and sizes configured for a particular implant location. For example, one or more surfaces of porous scaffold 4 may be curved with concave or convex curvature. Shapes that may be used include, but are not limited to, spheres, rods, discs, concave structures, convex structures, meshes, particles, matrices, and the like. In some examples, porous scaffold 4 may include a porous shape memory polymer that may have more than one shape depending on actuation.

Porous scaffold 4 may be composed of any biocompatible polymer capable of forming surfaces or structures that capture metastatic cells. In some examples, a biocompatible polymer is any polymer that is capable of remaining in the body for a length of time without significant adverse effects to the patient. Factors that may be used in selection of a biocompatible polymer may include, but are not limited to, biocompatibility, biodegradability, cell adhesion, healthy tissue migration, thermal conductivity, surface topology, biostability, rigidity, elasticity, and the like. Biocompatible polymers may include, but are not limited to: biopolymers, such as chitosan and starch; biodegradable polymers such as poly(lactide-co-glycolide) (PLG), poly(ε-caprolactone) (PCL), and polylactic acid (PLA); non-biodegradable polymers such as polyethylene (HDPE), polypropylene (PP), polytetrafluroethylene (PTFE), polymethylmethacrylate (PMMA), polydimethylsiloxane (PDMS), polyurethanes (PU), polyethylene glycol (PEG); and the like.

In some examples, porous scaffold 4 may include a release agent to promote capture of metastatic cells in or on porous scaffold 4. For example, porous scaffold 4 may include particles or dopants that may attract metastatic cells to porous scaffold 4 using chemical or biological agents, such as through adhesion or encapsulation. Release agents that may be used include, but are not limited to, proteins, carbohydrates, lipids, nucleic acids, and the like.

Electrically conductive or electrically semiconductive material 6 may be configured to generate heat to heat at least a portion of the volume of porous scaffold 4 in response to exposure an electromagnetic inductive stimulus. An electromagnetic inductive stimulus may include an alternating or oscillating magnetic field that induces currents in electrically conductive or electrically semiconductive material 6. For example, an alternating magnetic field may cause resistive heating in an electrically conductive material through eddy current losses or in an electrically semiconductive material through hysteresis losses. By using an electromagnetically inductive stimulus, electrically conductive or electrically semiconductive material 6 may apply heat to at least a portion of porous scaffold 4 indirectly without use of an invasive tool to output the heat or a need for continued invasive application of heat.

Electrically conductive or electrically semiconductive material 6 may include a variety of shapes and sizes. For example, as demonstrated in Example 1 below, an increase in the surface area of electrically conductive or electrically semiconductive material 6 may increase a temperature of the material. Shapes may include, but are not limited to, three-dimensional objects such as particles, spheres, cubes, cylinders, foams, and meshes; substantially two-dimensional objects such as discs and plates; and substantially one-dimensional objects such as rods, fibers, and wires. In some examples, electrically conductive or electrically semiconductive material 6 includes a substantially solid geometric shape. In some examples, electrically conductive or electrically semiconductive material 6 may include a foam or mesh that has pores or other surface modifications to increase the surface area of electrically conductive or electrically semiconductive material 6 for a given volume of electrically conductive or electrically semiconductive material 6. In other examples, electrically conductive or electrically semiconductive material 6 may include a plurality of distributed objects or particles throughout porous scaffold 4. For example, electrically conductive particles, a mesh, or a foam may be distributed throughout a volume of porous scaffold 4 to more evenly distribute heat through porous scaffold 4.

Electrically conductive or electrically semiconductive material 6 may include a variety of thicknesses. In some examples, electrically conductive or electrically semiconductive material 6 may be at least a thickness equal to a skin depth of the material form which electrically conductive or electrically semiconductive material 6 is formed. The skin depth of electrically conductive or electrically semiconductive material 6 may be the depth of electrically conductive or electrically semiconductive material 6 within which electric current flows upon exposure of electrically conductive or electrically semiconductive material 6 to an electromagnetic inductive stimulus. Factors affecting the skin depth of a material may include, but are not limited to, frequency of alternating magnetic current, material composition, and the like.

In some examples, electrically conductive or electrically semiconductive material 6 may have a thickness between 50 μm and 200 μm. For example, electrically conductive or electrically semiconductive material 6 may include aluminum, which may have a skin depth of about 100 μm, as seen in Table 3 in the Examples below, and a corresponding thickness of between about 100 μm and about 200 μm. As another example, electrically conductive or electrically semiconductive material 6 may include copper, which may have a skin depth of between about 136 μm, as seen in Table 3 in the Examples below, and a corresponding thickness of between about 100 μm and about 200 μm In some examples, electrically conductive or electrically semiconductive material 6 may have an average thickness of structural parts of electrically conductive or electrically semiconductive material 6 that is at least the thickness of skin depth of electrically conductive or electrically semiconductive material 6. For example, for electrically conductive or electrically semiconductive material 6 having a foam, branched, or particulate structure, each structure within electrically conductive or electrically semiconductive material 6, such as solid portion of foam (e.g., walls of the foam), a branch, or a particulate, may have an average thickness substantially equal to or greater than the skin depth of the material from which electrically conductive or electrically semiconductive material 6 is formed. By forming electrically conductive or electrically conductive material 6 substantially equal to or greater than a thickness of at least the skin depth, electrically conductive or electrically conductive material 6 may exhibit improved heating over a thickness that is less than the skin depth. Additionally, by forming electrically conductive or electrically conductive material 6 to a thickness substantially equal the skin depth, electrically conductive or electrically semiconductive material 6 may more efficiently heat porous scaffold 4 than a thickness that is greater than the skin depth.

Electrically conductive or electrically semiconductive material 6 may be composed of any material or materials capable of producing heat in response to the electromagnetic inductive stimulus. Factors that may be used in selection of a material for electrically conductive or electrically semiconductive material 6 may include, but are not limited to, biocompatibility, thermal conductivity, electrical conductivity, specific heat capacity, weight, and the like. Materials that may be used include, but are not limited to, non-biocompatible metals and alloys, such as copper, and aluminum; biocompatible metals and alloys, such as NiTi (nitinol), CoCrNi, titanium, and stainless steel; electrically conductive polymers, such as poly(thiophen) (PT), poly(3,4-ethylenedioxythiophene) (PEDOT), polyaniline (PANT), poly(acetylene) (PAC); and the like.

In some examples, the material used to fabricate electrically conductive or electrically semiconductive material 6 may not be biocompatible. To protect surrounding tissue from electrically conductive or electrically semiconductive material 6, implant 2 may include a coating 8 between electrically conductive or electrically semiconductive material 6 and porous scaffold 4. Coating 8 may surround electrically conductive or electrically semiconductive material 6 to prevent biological material from contacting electrically conductive or electrically semiconductive material 6 or material from electrically conductive or electrically semiconductive material from leaching out into porous scaffold 4. In some examples, coating 8 defines a thickness is between about 1 μm and about 50 μm.

Coating 8 may be a biocompatible coating composed of any biocompatible polymer that is capable of coating electrically conductive or electrically semiconductive material 6 for the duration of time implant 2 is implanted in a body of a patient. In some examples, coating 8 is composed of the same biocompatible polymer as porous scaffold 4. In some examples, coating 8 is composed of a biocompatible polymer that is less biodegradable than porous scaffold 4. Biocompatible polymers that may be used include, but are not limited to: biopolymers, such as chitosan and starch; biodegradable polymers such as poly(lactide-co-glycolide) (PLG), poly(ε-caprolactone) (PCL), and polylactide acid (PLA); non-biodegradable polymers such as polyethylene (HDPE), polypropylene (PP), polytetrafluroethylene (PTFE), polymethylmethacrylate (PMMA), polydimethylsiloxane (PDMS), polyurethanes (PU), polyethylene glycol (PEG); and the like.

Implant 2, which includes electrically conductive or electrically semiconductive material 6 surrounded by porous scaffold 4, may be used to capture and heat metastatic cancer cells. Implant 2 may be implanted in a body of a patient. After implantation, neighboring tissue cells and metastatic cancer cells may migrate into porous scaffold 4. An electromagnetic induction stimulus may be applied to the implant at a target strength and a target frequency for a target duration. The electromagnetic stimulus is selected to cause electrically conductive or electrically semiconductive material 6 to heat at least a portion of the porous scaffold to at least a target temperature. The target temperature may be selected to kill the metastatic cancer cells, and in some examples, may be selected to not cause significant harm to cells surrounding implant 2.

Figure 2:
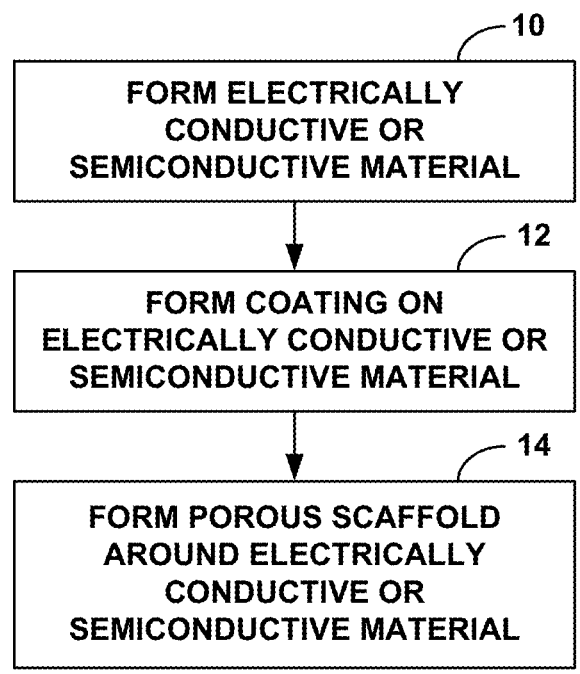
FIG. 2 is a conceptual flow diagram of an example technique for manufacturing an implant for capturing and heating metastatic cancer cells.

FIG. 2 is a conceptual flow diagram of an example technique for manufacturing an implant for capturing and heating metastatic cancer cells, such as implant 2 of FIG. 1. FIG. 2 may be described with reference to FIG. 1. However, FIG. 2 may be used to form other implants with different structure compared to that shown in FIG. 1.

The technique of FIG. 2 may optionally include forming electrically conductive or electrically semiconductive material 6 (10). For example, electrically conductive or electrically semiconductive material 6 may be formed into a shape that has a high surface area, such as a disc. A higher surface area may increase the amount of resistive heating from eddy currents induced by the electromagnetic inductive stimulus. In other examples, electrically conductive or electrically semiconductive material 6 may be formed into a shape that has branches, pores, or other structures that increase the surface area. In some examples, electrically conductive or electrically semiconductive material may be structured, such as by distributed particles, foam, or a mesh, so that, after formation of porous scaffold 4, electrically conductive or electrically semiconductive material 6 is disposed substantially throughout a volume of porous scaffold 4.

The technique of FIG. 2 also may optionally include forming a coating 8 that includes a biocompatible polymer on electrically conductive or electrically semiconductive material 6 (12). Techniques for coating may include, but are not limited to, dipping, spraying, polymerization, and the like. A variety of precursors may be used to form coating 8, including monomers, particles, or polymers of: biopolymers, such as chitosan and starch; biodegradable polymers such as poly(lactide-co-glycolide) (PLG), poly(ε-caprolactone) (PCL), and polylactide acid (PLA); non-biodegradable polymers such as polyethylene (HDPE), polypropylene (PP), polytetrafluroethylene (PTFE), polymethylmethacrylate (PMMA), polydimethylsiloxane (PDMS), polyurethanes (PU), polyethylene glycol (PEG); and the like.

The technique of FIG. 2 includes forming porous scaffold 4 comprising a biocompatible polymer around electrically conductive or electrically semiconductive material 6 (14). Porous scaffold 4 may define pores configured to capture metastatic cancer cells. Porous scaffold 4 may be formed by a variety of methods including, but not limited to, polymerization, solvent casting, melt molding, fiber bonding, gas foaming, phase separation, electrospinning, porogen or template leaching, fiber meshing, membrane lamination, and the like. A variety of precursors may be used to form porous scaffold 4, including monomers, particles, or polymers of: biopolymers, such as chitosan and starch; biodegradable polymers such as poly(lactide-co-glycolide) (PLG), poly(ε-caprolactone) (PCL), and polylactide acid (PLA); non-biodegradable polymers such as polyethylene (HDPE), polypropylene (PP), polytetrafluroethylene (PTFE), polymethylmethacrylate (PMMA), polydimethylsiloxane (PDMS), polyurethanes (PU), polyethylene glycol (PEG); and the like.

Figure 3:
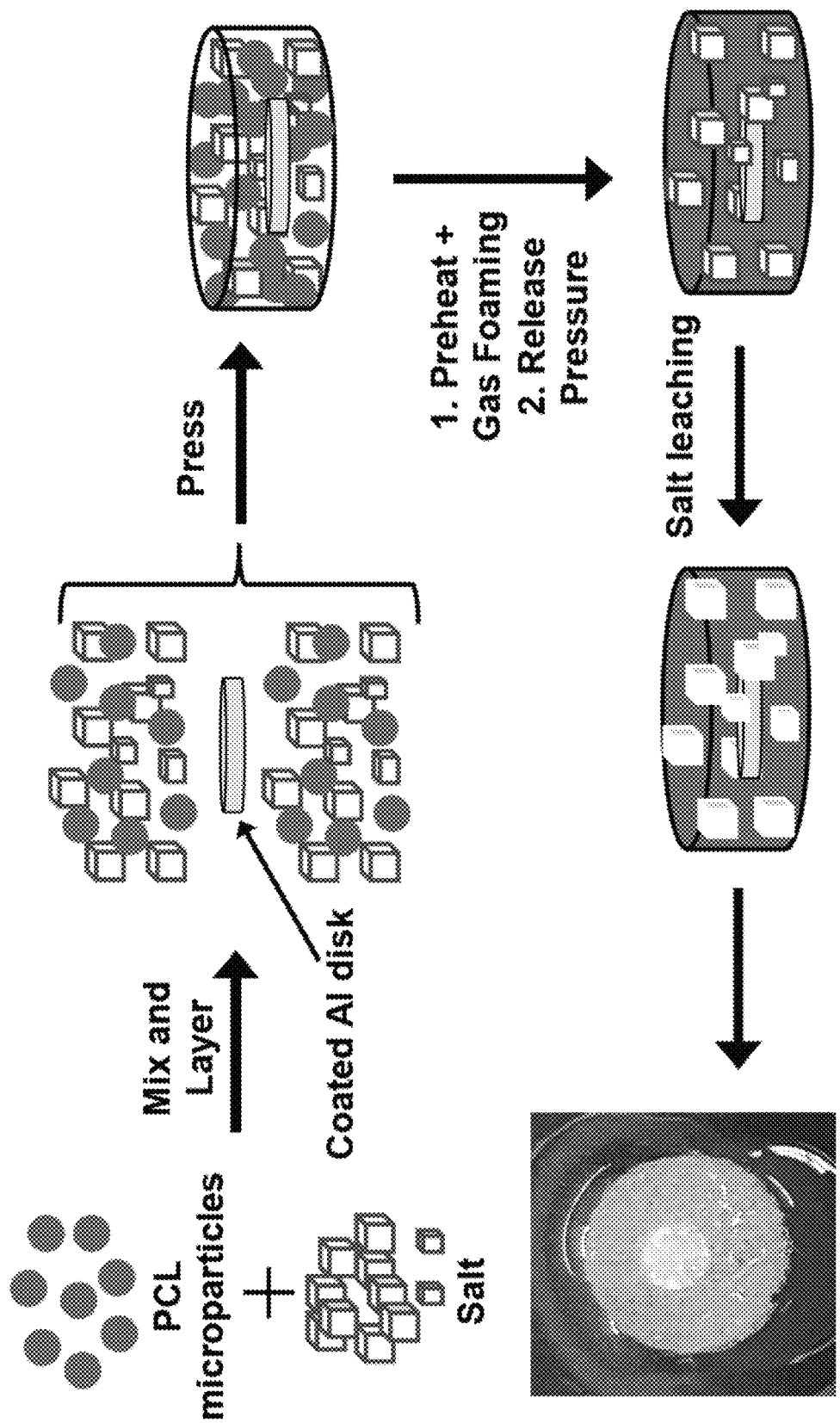
FIG. 3 is a diagram of an example technique for forming a porous scaffold around an electrically conductive or electrically semiconductive material.

FIG. 3 is an example diagram of a process for forming a porous scaffold around an electrically conductive or electrically semiconductive material. The process of FIG. 3 may be used, for example, in Example 3 below. The process of FIG. 3 may include creating a scaffold medium that includes a first biocompatible polymer and a template medium. In this example, the first biocompatible polymer includes PCL microparticles and the template medium includes salt particles. The template medium size may be selected according to the desired pore size. For example, a particular pore size of the porous scaffold may correspond to a substantially similar salt particle size, a particular average porosity may correspond to a particular concentration or average salt particle size, or the like.

The electrically conductive or electrically semiconductive material may be coated with the scaffold medium. In this example, the electrically conductive or electrically semiconductive material is a coated aluminum disk. The coating on the coated aluminum disk may include a second biocompatible polymer. In some examples, the scaffold medium is a liquid or gel that coats the electrically conductive or electrically semiconductive material, while in other examples, the scaffold medium is a solid that contacts at least a portion of the electrically conductive or electrically semiconductive material. In some examples that include particles of electrically conductive or electrically semiconductive materials, the particles may be distributed in a volume of the scaffold medium to coat the particles. In some examples, other additives, such as releasing agents or thermally conductive particles, may be introduced to the scaffold medium before curing.

Once the scaffold medium has coated the electrically conductive or electrically semiconductive material, the scaffold medium may be cured around the electrically conductive or semiconductive material. In this example, curing includes pressing the scaffold medium around the electrically conductive or electrically semiconductive material, heating the scaffold medium, and foaming the scaffold medium. In other examples, curing the scaffold medium may include initiating polymerization or crosslinking, melting and cooling the biocompatible polymer, or the like.

Once the scaffold medium has cured, the template medium may be removed from the scaffold medium to form pores in the porous scaffold. In this example, the salt may be dissolved or leached with a solvent.

Figure 4:
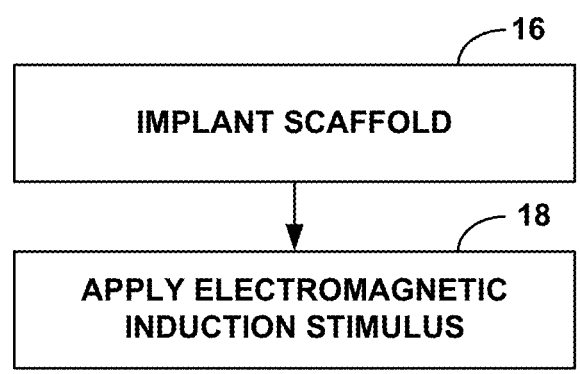
FIG. 4 is a conceptual flow diagram of an example technique for capturing and heating metastatic cancer cells in tissue.

FIG. 4 is a conceptual flow diagram of an example method for capturing and heating metastatic cancer cells in tissue. FIG. 4 may be described with reference to FIG. 1. The method of FIG. 4 includes implanting implant 2 in a body of a patient (16). Implant 2 may be implanted at a variety of locations where metastatic cancer cells may migrate, such as liver, lungs, bones, and lymph nodes. Implanting may be performed using, for example, catheter, syringe, incision, and the like. As an example, a surgeon may make an incision in an area of the body of the patient with a high likelihood of metastasis, and place implant 2 subcutaneously in the area of the body.

The method of FIG. 4 includes applying an electromagnetic stimulus to the implant (18). The electromagnetic induction stimulus may be selected to cause electrically conductive or electrically semiconductive material 6 to heat at least a portion of porous scaffold 4 to at least a target temperature. The target temperature may be selected to kill the captured metastatic cancer cells without causing significant harm to healthy tissue in and around implant 2. In some examples, the electromagnetic induction stimulus is selected to cause electrically conductive or electrically semiconductive material 6 to heat substantially all of porous scaffold 4 to at least the target temperature. In some examples, the target temperature is between about 40 degrees Celsius and about 50 degrees Celsius. In some examples, the target temperature is selected to kill metastatic cells up to a selected distance from a surface of the electrically conductive or electrically semiconductive material 6, such as at least 2 mm.

The electromagnetic induction stimulus may be applied at a target strength and a target frequency for a target duration, for example, using an alternating magnetic field such as a radiofrequency coil. As the strength, frequency, and duration of the electromagnetic induction stimulus increase, a temperature of electrically conductive or electrically semiconductive material 6 may increase. In some examples, the strength and frequency of the electromagnetic induction stimulus may be tuned by the surface area of electrically conductive or electrically semiconductive material 6. In some examples, the target strength may be between about 10 kA/m and about 100 kA/m. In some examples, the target frequency may be between about 100 kHz to about 500 kHz. In some examples, the target duration may be between about one minute and about ten minutes. In some examples, the electromagnetic induction stimulus may be applied in pulses or periods. In some examples, the target strength, the target frequency, the target duration, and the target temperature are selected to kill at least 85% of metastatic cells in porous scaffold 4. In some examples, the target strength, the target frequency, the target duration, and the target temperature are selected to kill substantially all metastatic cells in porous scaffold 4.

In some examples, a target strength, target frequency, and/or target duration may be selected to create a specific absorption rate (SAR). The SAR may represent a measure of the amount of energy being delivered to the surrounding tissue. In some examples, the target strength, target frequency, and/or target duration may be selected to achieve an SAR of at least about $1 \times 10^8$ W/m³.

In some examples, death of metastatic cancer cells may be correlated with a degree of protein denaturation resulting from the application of the electromagnetic stimulus. For example, a protein denaturation of greater than 10% may be correlated with a 90% drop in cell viability. In some examples, a target strength, target frequency, and target duration may be selected to achieve a minimum threshold of protein denaturation associated with substantial death of metastatic cancer cells. For examples, a 10 minute treatment of 15 kA/m at 360 kHz may create a 15% protein denaturation ring around porous scaffold 4.

Select examples of the present disclosure include, but are not limited to, the following:

A first example provides a method comprising forming a porous scaffold comprising a biocompatible polymer around an electrically conductive or electrically semiconductive material, wherein the porous scaffold defines pores configured to capture metastatic cancer cells.

A second example provides the method of the first example, wherein the biocompatible polymer comprises a first biocompatible polymer, and wherein the method further comprises forming a coating comprising a second biocompatible polymer on the electrically conductive or electrically semiconductive material before forming the porous scaffold around the electrically conductive or electrically semiconductive material.

A third example provides the method of the second example, wherein forming the porous scaffold further comprises: coating the electrically conductive or electrically semiconductive material with a scaffold medium that includes the first biocompatible polymer and a template material; curing the scaffold medium around the electrically conductive or electrically semiconductive material; and removing the template material to form the pores.

A fourth example provides the method of the third claim, wherein curing the scaffold medium further includes pressing the scaffold medium around the electrically conductive or electrically semiconductive material; heating the scaffold medium; and foaming the scaffold medium.

A fifth example provides the method of the third or fourth examples, wherein the template material comprises a salt, and wherein removing the template material comprises dissolving the salt in a solvent.

A sixth example provides the method of any one of first through fifth examples, wherein the electrically conductive or electrically semiconductive material is substantially two-dimensional.

A seventh example provides the method of any one of first through fifth examples, wherein the electrically conductive or electrically semiconductive material comprises a metal.

An eighth example provides the method of the seventh example, wherein the electrically conductive or electrically semiconductive material comprises a biocompatible metal.

A ninth example provides the method of the seventh example, wherein the electrically conductive or electrically semiconductive material comprises a non-biocompatible metal.

A tenth example provides the method of the seventh example, wherein the electrically conductive or electrically semiconductive material comprises at least one of stainless steel, titanium, aluminum, or copper.

An eleventh example provides the method of any one of the first through tenth examples, wherein the electrically conductive or electrically semiconductive material comprises a substantially solid geometric shape.

A twelfth example provides the method of any one of first through tenth examples, wherein the electrically conductive or electrically semiconductive material comprises at least one of a foam, a mesh, or a plurality of particles.

A thirteenth example provides the method of the twelfth example, wherein the electrically conductive or electrically semiconductive material is disposed substantially throughout a volume of the porous scaffold.

A fourteenth example provides the method of any one of the first through thirteenth examples, wherein the biocompatible polymer comprises at least one of poly(lactide-co-glycolide) or polycaprolactone.

A fifteenth example provides a device, comprising: an electrically conductive or electrically semiconductive material; and a biocompatible porous scaffold around the electrically conductive or electrically semiconductive material, wherein the biocompatible porous scaffold comprises a biocompatible polymer and pores configured to capture metastatic cells.

A sixteenth example provides the device of the fifteenth example, further comprising a biocompatible coating between the electrically conductive or electrically semiconductive material and the porous scaffold.

A seventeenth example provides the device of the sixteenth example, wherein the biocompatible coating comprises at least one of polycaprolactone or poly(lactic acid).

An eighteenth example provides the device of the sixteenth or seventeenth examples, wherein the biocompatible coating defines a thickness is between about 1 μm and about 50 μm.

A nineteenth example provides the device of any one of the fifteenth through eighteenth examples, wherein the electrically conductive or electrically semiconductive material is substantially two-dimensional.

A twentieth example provides the device of any one of the fifteenth through nineteenth examples, wherein the electrically conductive or electrically semiconductive material comprises a metal.

A twenty-first example provides the device of the twentieth example, wherein the electrically conductive or electrically semiconductive material comprises a biocompatible metal.

A twenty-second example provides the device of the twentieth example, wherein the electrically conductive or electrically semiconductive material comprises a non-biocompatible metal.

A twenty-third example provides the device of the twentieth example, wherein the electrically conductive or electrically semiconductive material comprises at least one of stainless steel, titanium, aluminum, or copper.

A twenty-fourth example provides the device of any one of fifteenth through twenty-third examples, wherein the electrically conductive or electrically semiconductive material comprises a substantially solid geometric shape.

A twenty-fifth example provides the device of any one of the fifteenth through twenty-third examples, wherein the electrically conductive or electrically semiconductive material comprises at least one of a foam, a mesh, or a plurality of particles.

A twenty-sixth example provides the device of the twenty-fifth example, wherein the electrically conductive or electrically semiconductive material is disposed substantially throughout a volume of the porous scaffold.

A twenty-sixth example provides the device of any one of the fifteenth through twenty-sixth examples, wherein the biocompatible polymer comprises at least one of poly(lactide-co-glycolide) or polycaprolactone.

A twenty-eighth example provides the device of any one of the fifteenth through twenty-seventh examples, wherein the electrically conductive or electrically semiconductive material has a thickness between about 50 µm and about 150 µm.

A twenty-ninth example provides the device of any one of the fifteenth through twenty-eighth examples, wherein the electrically conductive or electrically semiconductive material has a thickness of at least a skin depth of the electrically conductive or electrically semiconductive material.

A thirtieth example provides the device of any one of the fifteenth through twenty-eighth examples, wherein the electrically conductive or electrically semiconductive material has a thickness substantially equal to a skin depth of the electrically conductive or electrically semiconductive material.

A thirty-first example provides the device of any one of the fifteenth through thirtieth examples, wherein the electrically conductive or electrically semiconductive material comprises a metal foam, wherein walls of the metal foam have an average thickness substantially equal to a skin depth of the electrically conductive or electrically semiconductive material.

A thirty-second example provides a method, comprising: implanting the device of any one of the fifteenth through thirty-first examples in a body of a patient; and applying an electromagnetic induction stimulus to the device at a target strength and target frequency for a target duration, wherein the electromagnetic induction stimulus is selected to cause the electrically conductive or electrically semiconductive material to heat at least a portion of the porous scaffold to at least a target temperature.

A thirty-third example provides the method of the thirty-second example, further comprising selecting the target strength, the target frequency, the target duration, and the target time to cause the electrically conductive or electrically semiconductive material to resistively heat the metastatic cells to kill at least 85% of metastatic cells in the porous scaffold.

A thirty-fourth example provides the method of the thirty-second example, wherein the target temperature is between 40 degrees Celsius and 50 degrees Celsius.

A thirty-fifth example provides the method of any one of the thirty-second through thirty-fourth examples, wherein the target duration is between about one minute and about ten minutes.

A thirty-sixth example provides the method of any one of the thirty-second through thirty-fifth examples, wherein the target strength is between about 10 kA/m and about 100 kA/m, and the target frequency is between about 100 kHz and about 500 kHz.

A thirty-seventh example provides the method of any one of the thirty-second through thirty-sixth examples, wherein electromagnetic induction stimulus is selected to cause the electrically conductive or electrically semiconductive material to heat substantially all of the porous scaffold to at least the target temperature.

A thirty-eighth example provides the method of any one of the thirty-second through thirty-seventh examples, wherein the target temperature is selected to kill metastatic cells up to about 2 mm from a surface of the electrically conductive or electrically semiconductive material.

A thirty-ninth example provides the method of any one of the thirty-second through thirty-eighth examples, further comprising selecting the target strength, the target frequency, the target duration, and the target time to cause the electrically conductive or electrically semiconductive material to resistively heat the metastatic cells to kill substantially all metastatic cells in the porous scaffold.

A fortieth example provides the method of any one of the thirty-second through thirty-ninth examples, wherein the electromagnetic induction stimulus is selected to cause the electrically conductive or electrically semiconductive material to cause at least about 15% protein denaturation around the device.

A forty-first example provides the method of any one of the thirty-second through fortieth examples, wherein the electromagnetic induction stimulus is selected to cause the electrically conductive or electrically semiconductive material to create a specific absorption rate of at least about $3 \times 10^8$ W/m$^3$.

EXAMPLES

Example 1: Electrically Conductive Material Fabrication and Coating

An electrically conductive or electrically semiconductive material may be fabricated from metal disks using a variety of methods. In this example, metal disks were made using a custom punch on a 0.1 mm thick Puratronic® aluminum foil (available from Alfa Aesar, Tewksbury, Massachusetts) or 0.1 mm thick Puratronic® copper foil (available from Alfa Aesar). Four different sized punches were used to create metal disks of different sizes. Following fabrication, disk size was measured through image analysis using ImageJ.

Figure 5A:
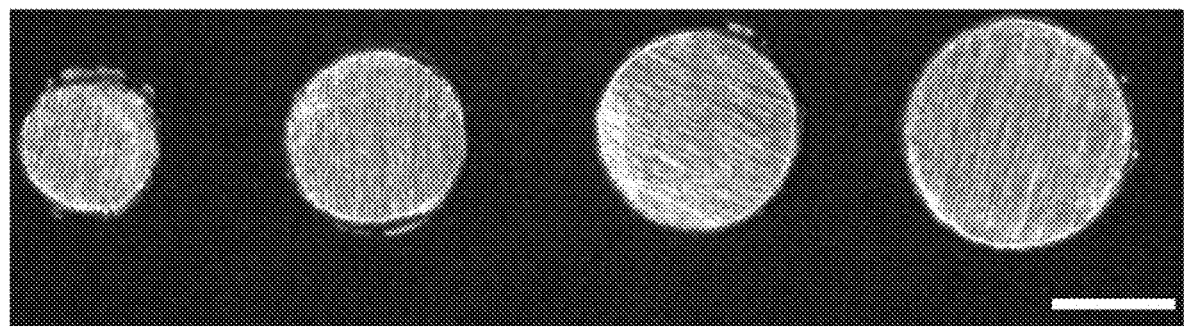
FIG. 5A illustrates metal disks of various diameters that were fabricated using a hand punch.
Figure 5B:
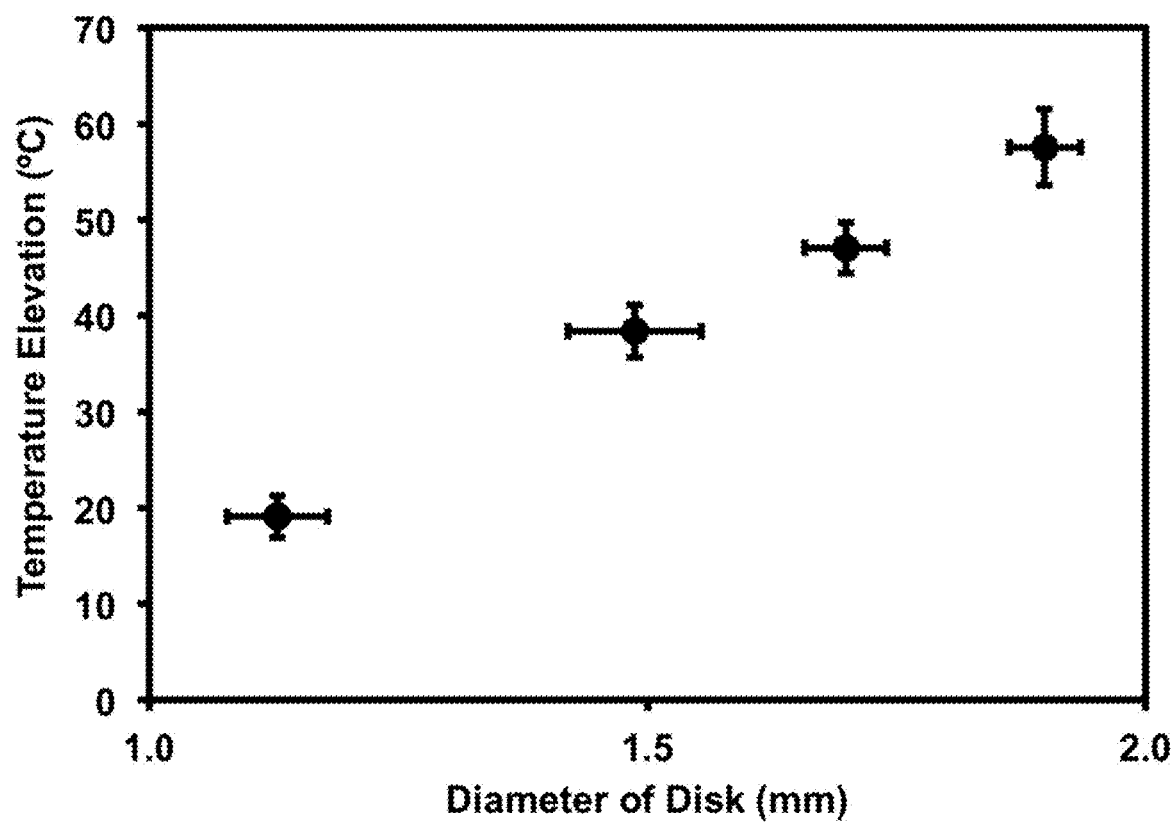
FIG. 5B illustrates temperature elevation resulting from placement of aluminum disks of various sizes in an alternating magnetic field with a strength of 15 kA/m and a frequency of 360 kHz.
Figure 5C:
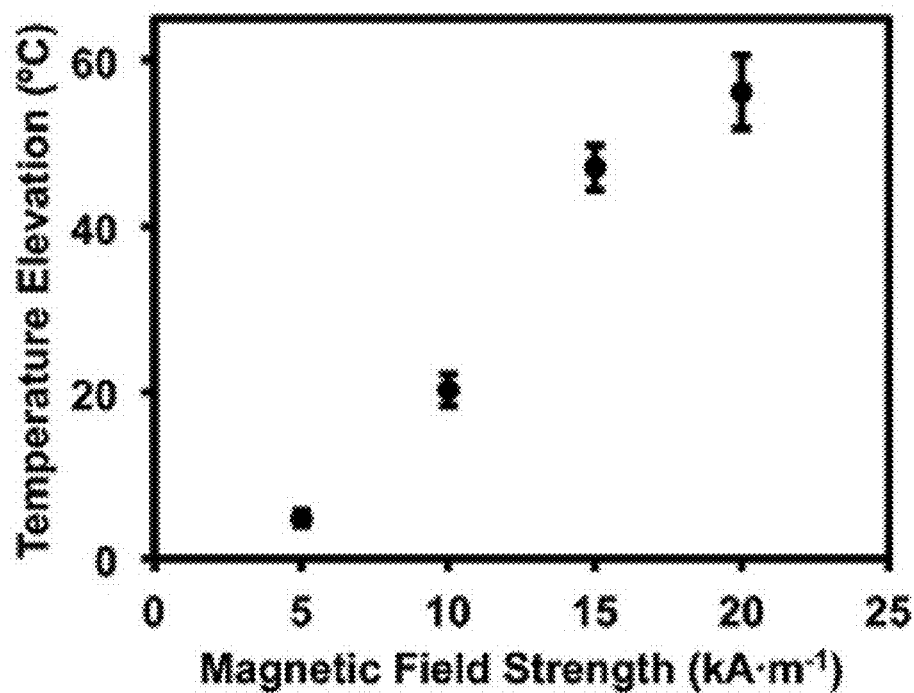
FIG. 5C illustrates an effect of increasing magnetic field strength from 5 kA/m to 20 kA/m with a frequency of 360 kHz on temperature elevation of aluminum disks with a diameter of 1.70±0.04 mm.
Figure 5D:
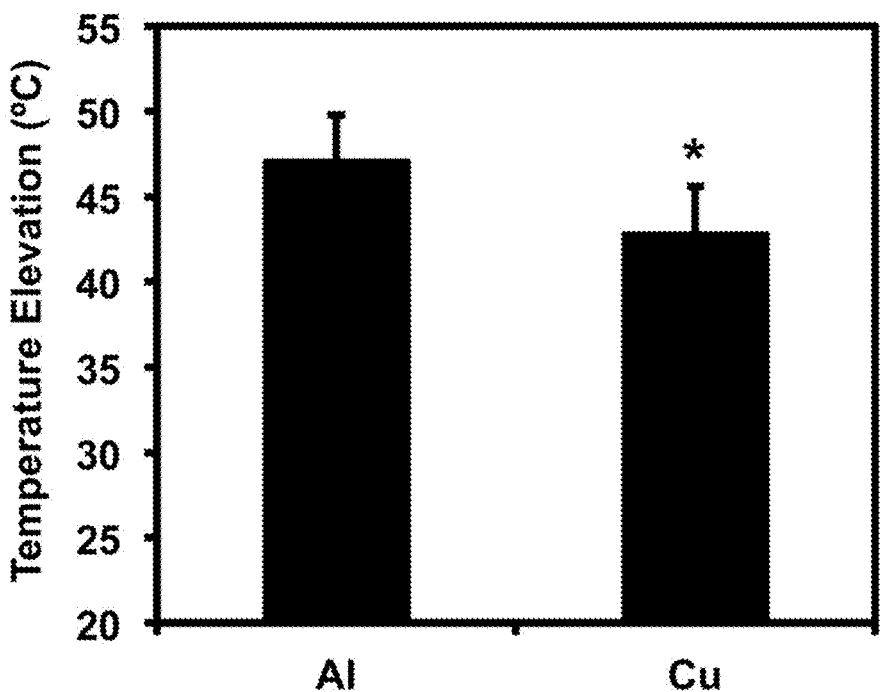
FIG. 5D illustrates an effect of changing metal composition from aluminum to copper on temperature elevation of metal disks (1.70±0.04 mm and 1.67±0.07 mm diameter for aluminum and copper disks, respectively) using a magnetic field with a strength of 15 kA/m and a frequency of 360 kHz.

FIGS. 5A-D illustrate structures and properties of an electrically conductive material in the form of metal disks for tunable inductive heating of the metal disks using an electromagnetic induction stimulus in the form of an alternating magnetic field. FIG. 5A illustrates metal disks of various diameters that were fabricated using a hand punch. Scale bar indicates 1 mm. FIG. 5B illustrates temperature elevation resulting from placement of aluminum disks of various sizes in an alternating magnetic field with a strength of 15 kA/m and a frequency of 360 kHz. FIG. 5C illustrates an effect of increasing magnetic field strength from 5 kA/m to 20 kA/m with a frequency of 360 kHz on temperature elevation of aluminum disks with a diameter of 1.70±0.04 mm. FIG. 5D illustrates an effect of changing metal composition from aluminum (1.70±0.04 mm diameter) to copper (1.67±0.07 mm diameter) on temperature elevation of disks using a magnetic field with a strength of 15 kA/m and a frequency of 360 kHz.

Inductive heating through an oscillating magnetic field may require a thermal seed, such as electrically conductive or electrically semiconductive material, that has the ability to heat in response to the presence of an oscillating magnetic field. Metal disks of various diameters, as in FIG. 5A, were placed in a radiofrequency coil and an oscillating magnetic field with strength 15 kA·m$^{-1}$ and a frequency of 360 kHz was applied. As the diameter of the disk increased from 1.13±0.05 mm to 1.90±0.04 mm, the temperature elevation achieved increased from 17.6±1.33° C. to 55.3±3.44° C., as seen in FIG. 5B. With the disk diameter fixed at 1.70±0.04 mm, the temperature elevation may also be modulated by the strength of the magnetic field, with a 4.8±0.9° C., 20.3±1.9° C., 47.1±2.6° C., and 56.2±4.4° C. elevation achieved with a field strength of 5, 10, 15, and 20 kA/m, respectively, as seen in FIG. 5C. The type of metal used may also impact heat generation; at a field strength of 15 kA·m$^{-1}$ and a frequency of 360 kHz, aluminum and copper disks of the same diameter achieve temperature increases of 47.7±2.1° C. and 42.8±1.7° C., respectively, as seen in FIG. 5D. These data demonstrate that metal disks are effective thermal seeds for generating a sufficient temperature increase for short hyperthermia treatment of cancer cells, and this approach is applicable to metals other than aluminum.

Figure 5E:
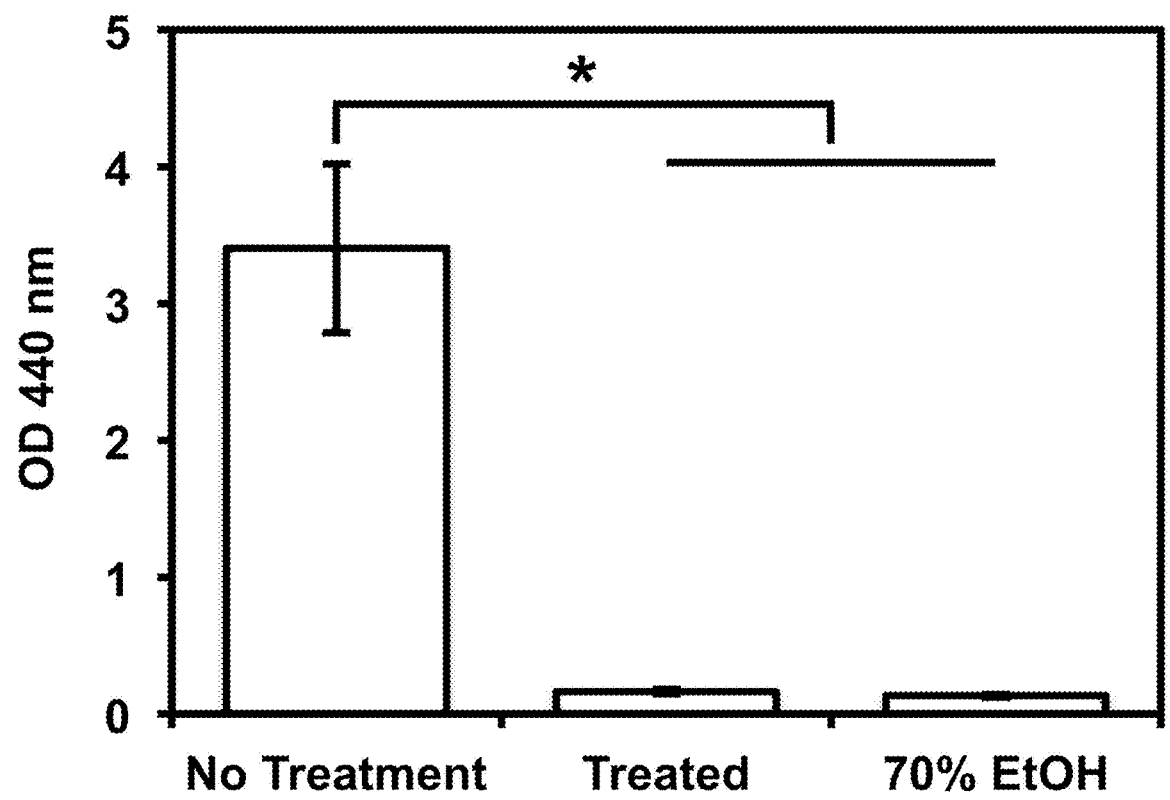
FIG. 5E is a graph of in vitro ablation of 4T1 cancer cells by induction heating.

For verification that the chosen treatment conditions could kill breast cancer cells, 4T1 cells were encapsulated in Matrigel surrounding a 1.70 mm Al disk. FIG. 5E is a graph of in vitro ablation of 4T1 cancer cells by induction heating. WST-1 viability assay performed on 4T1 cells encapsulated in Matrigel surrounding a 1.70 mm Al disk before and after treatment with an oscillating magnetic field at 15 kA·m$^{-1}$ at 360 kHz for 10 min. As a positive control for cell death, samples treated with 70% ethanol were evaluated. (*) P<0.001 compared to no treatment. Viability data is mean±SD, n=3. Using the same magnetic field strength, frequency, and duration as in the treatment of tissue-laden PCL-Al scaffolds, 4T1 cancer cells were successfully ablated, as evidenced by a substantial decrease in viability shown in FIG. 5E. Taken together, these findings show that induced focal thermal ablation can effectively kill cells in the scaffold ex vivo and these parameters can also be applied to kill breast cancer cells in vitro. Additionally, the results correlate with the developed cell death model, indicating that the model has predictive capabilities in optimizing treatment conditions.

Example 2: Coating of Metal Disks

Metal disks may be coated to impart biocompatibility to the metal disk. To coat the metal disks with a polymer film, the disks were dipped once into an 10% (w/w) solution of poly(ε-caprolactone) (DURECT; inherent viscosity=0.65-0.85 dL/g) in dichloromethane. Coated disks were dried overnight. To characterize the polymer coating thickness, partial removal of the coating was performed using a razor blade, and step height across the interface of the coated and uncoated regions was measured using a Tencor P10 profilometer.

Figure 6A:
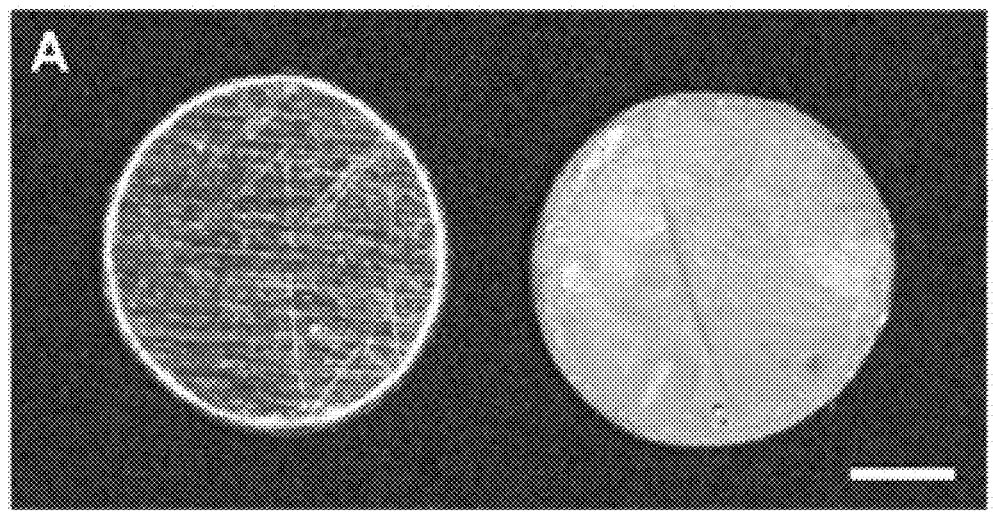
FIG. 6A illustrates images of an uncoated (left) and PCL-coated (right) aluminum disk.
Figure 6B:
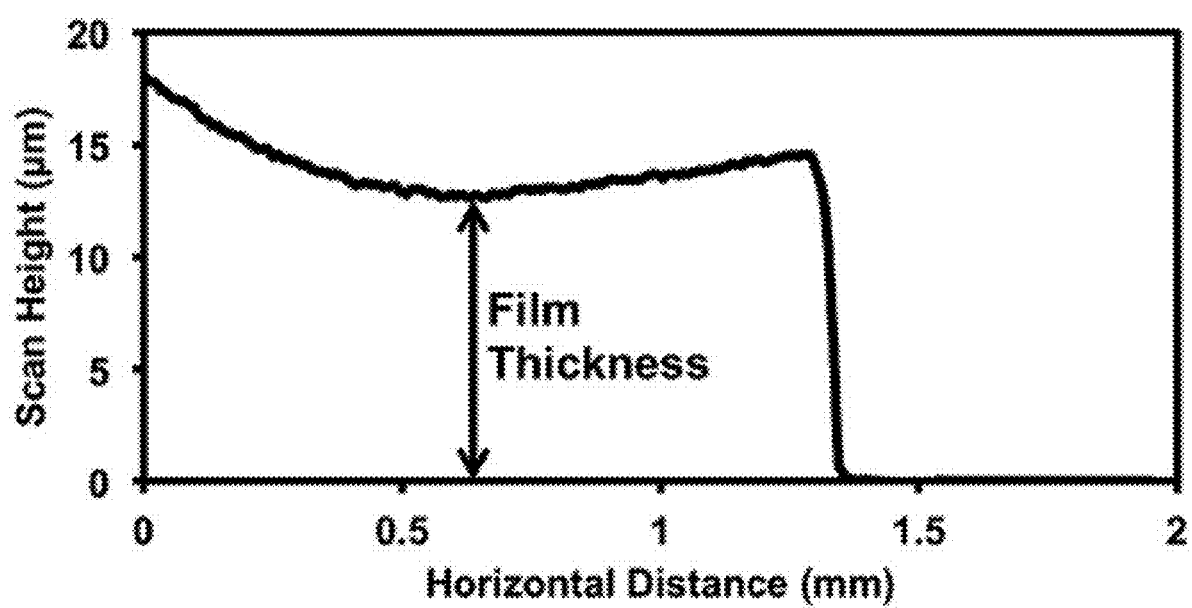
FIG. 6B illustrates a profilometer scan across the middle of the partially coated and uncoated disk of FIG. 6C.
Figure 6C:
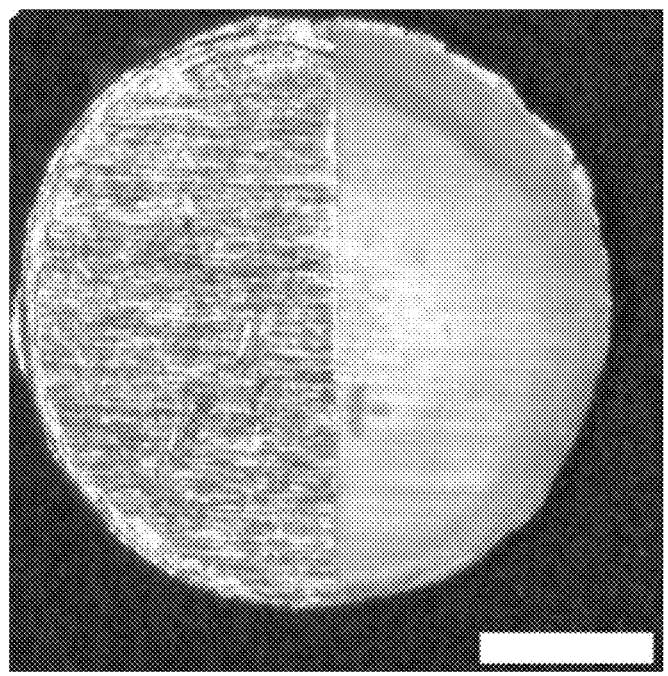
FIG. 6C illustrates an image of the partially coated and partially uncoated disk.
Figure 6D:
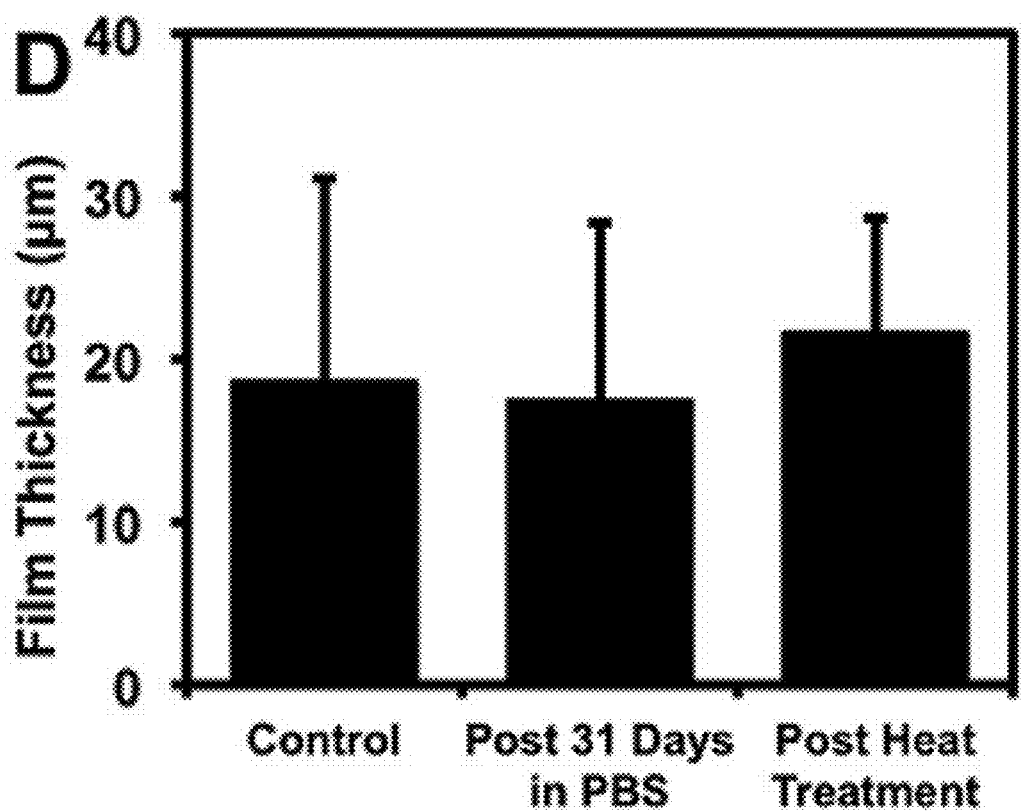
FIG. 6D illustrates a film thickness of the disk of FIG. 6C before and after an incubation period in PBS at 37° C. for 31 days.

FIGS. 6A and 6B illustrate structures and measurements of a coating of a metal surface of a metal disk with a biocompatible polymer film. FIG. 6A illustrates images of an uncoated (left) and PCL-coated (right) aluminum disk. Scale bar indicates 1 mm. FIG. 6B illustrates an average PCL film thickness of the coating before and after exposure to PBS at 37° C. for 31 days or to heat treatment at 15 kA/m, 360 kHz for 10 minutes. FIG. 6C illustrates an image of the partially coated and partially uncoated disk. FIG. 6D illustrates a film thickness of the disk of FIG. 6C before and after an incubation period in PBS at 37° C. for 31 days.

Example 3: Porous Scaffold Fabrication

Porous scaffolds may be formed from biocompatible polymers using techniques that give the composite scaffold a particular porosity. Since aluminum is not biocompatible, the aluminum metal disks were first coated with a PCL film, which exhibited a thickness of 18.6±12.4 as seen in FIG. 6A. To form porous scaffolds, PCL microspheres were first prepared as previously described. In this example, a 6% (w/w) solution of poly(ε-caprolactone) (DURECT; inherent viscosity=0.65-0.85 dL·g$^{-1}$) in dichloromethane was emulsified in a 10% poly(vinyl alcohol) solution and homogenized at 10,000 rpm for 1 minute. Microspheres were lyophilized for 48 hours. PCL microspheres and sieved sodium chloride particles (250-425 μm) were mixed in a 1:30 (w/w) ratio. PCL-coated metal disks were layered between two PCL microsphere/sodium chloride mixtures in a 5 mm steel die (Specac), and the contents were pressed to 3,300 lb for 45 seconds. The pressed disks were heated at 60° C. for 5 minutes on each side followed by foaming at 800 psig for ~24 hours to fuse together the polymer microspheres. Salt particles were removed by immersing disks in water for 90 minutes. Porous scaffolds were sterilized by soaking 70% ethanol followed by rinsing in sterile water and drying on a sterile gauze pad.

Example 4: Scaffold Implantation

Animal studies were performed in accordance with institutional guidelines and protocols approved by the University of Minnesota Institutional Animal Care and Use Committee (IACUC). BALB/c mice were purchased from The Jackson Laboratory, and mice were 8-31 weeks of age at the time of surgery. Two scaffolds were implanted into the subcutaneous space of the upper dorsal region per mouse. Scaffolds were removed 3-4 weeks following implantation.

Example 5: Tissue Sectioning and Histological Analysis

Tissue-laden scaffolds for histology were removed from the subcutaneous space 3-4 weeks post-implantation. The tissues were fixed in 10% buffered formalin, embedded in paraffin, sectioned at 4 μm using an HM 310 microtome (Microm). Slides were stained with hematoxylin and eosin. Apoptosis analysis was performed using an ApopTag® Peroxidase In Situ Apoptosis Detection Kit (EMD Millipore S7100). Slides were imaged using an EVOS FL Auto Microscope (ThermoFisher Scientific).

Figure 9A:
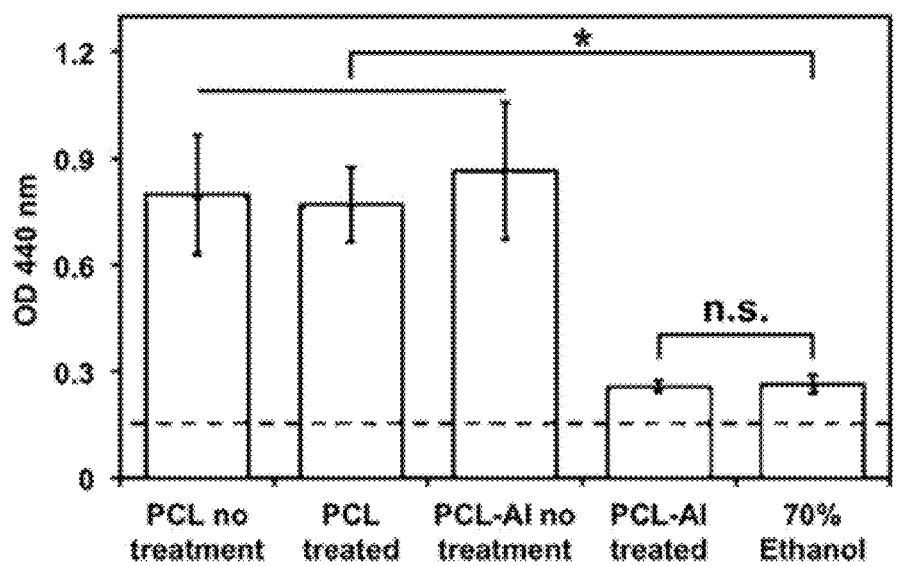
FIG. 9A illustrates a viability assay of cells in tissue-laden scaffolds with and without ex vivo treatment.
Figure 9B:
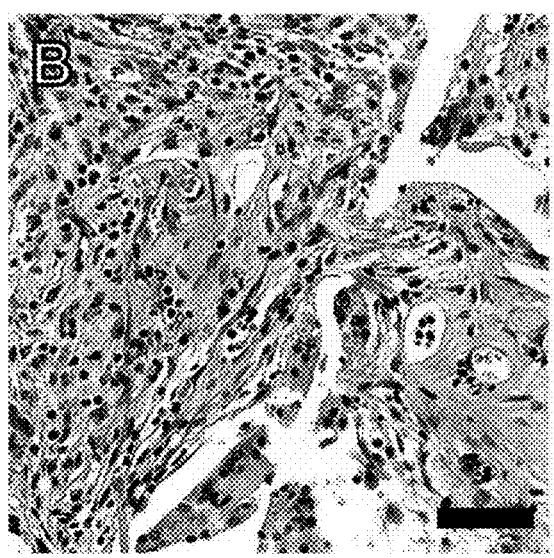
FIG. 9B illustrates a section of a tissue-laden PCL scaffold following ex vivo treatment.
Figure 9C:
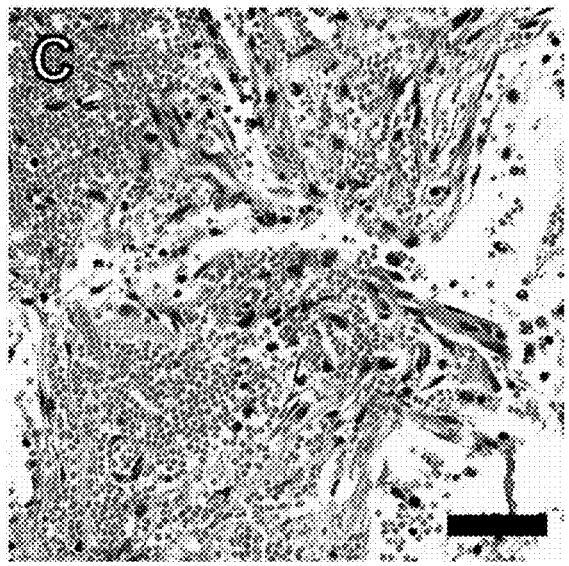
FIG. 9C illustrates a section of a tissue-laden PCL-Al scaffold following ex vivo treatment.

FIGS. 9B and 9C illustrate sections of a tissue-laden PCL scaffold (FIG. 9B) and PCL-Al scaffold (FIG. 9C) following ex vivo treatment. As shown in FIGS. 9B and 9C, hematoxylin and eosin staining demonstrated no histological differences between PCL scaffolds and PCL-Al composite scaffolds. TUNEL staining showed that there was no observable increase in the presence of apoptotic cells in the PCL-Al composite scaffolds compared to metal-free PCL scaffolds. These results demonstrate that the PCL-Al composite scaffolds are biocompatible.

H&E stained sections showed no signs of cytotoxicity in PCL-Al scaffolds as compared to PCL scaffolds, with PCL and PCL-Al tissue-laden scaffolds showing no quantifiable, statistical difference in the density of multinucleated cells, fibroblasts, new blood vessel formation, and inflammatory infiltrates by pathological scoring, as shown in Table 1 below. These data demonstrate that the PCL-Al composite scaffolds are as biocompatible as unmodified PCL scaffolds in vivo.

TABLE 1

Pathologist Scoring of Tissue-Laden Composite Scaffolds

| Density of | Scaffold Type | Average Scoring (0-3) | Standard Deviation |
|---|---|---|---|
| Multinucleated Cell | PCL | 2.3 | 0.6 |
|  | PCL-Al | 1.7 | 0.9 |
| Fibroblast | PCL | 2.4 | 0.5 |
|  | PCL-Al | 1.8 | 1.1 |
| New Blood Vessel Formation | PCL | 2.3 | 0.3 |
|  | PCL-Al | 1.9 | 1.0 |
| Inflammatory Infiltrate | PCL | 2.6 | 0.2 |
|  | PCL-Al | 1.9 | 0.5 |

Example 6: Density Measurements

Density of tissue-laden scaffolds was calculated by dividing the measured mass by the volume. The geometry of the scaffold was approximated to be cylindrical, and the volume (V) was calculated by measuring the diameter (d) and height (h) using digital calipers and using the formula:

$$V = \frac{\pi d^2 h}{4}$$

The computed density is shown in Table 2 below.

TABLE 2

Thermal Properties of Tissue-laden Scaffolds

| Property | Value |
|---|---|
| Density ($\rho$) (g · mL$^{-1}$) | 1.06 |
| Specific Heat Capacity ($C_P$) (J · g$^{-1}$ · K$^{-1}$) | 0.0232 · T(° C.) + 2.5008 |
| Thermal Conductivity (k) (W · m$^{-1}$ · K$^{-1}$) | −0.0005 · T(° C.) + 0.5077 |

Example 7: Thermal Conductivity Measurements

An experimental setup based on the bi-directional 3ω method was employed to measure the thermal conductivity of the samples. The sensor was a thin heater line (2.5 mm×40 μm) microfabricated on glass substrate. The electrical resistance of the sensor was calibrated to measure temperature. Further, the sensor was calibrated for its thermal conductivity using the traditional 3ω method. To measure thermal conductivity, the output 3ω voltage (V3ω) was measured as a function of heater electrical frequency (~0.5 to 10 Hz) and the slope (dV3ω/d(ln ω)) was used to determine thermal conductivity. During sample measurement, the tissue was sliced into approximately 2 mm long samples and placed on the heater line. To reduce dehydration and/or evaporation of water content in the tissue, the sample was encapsulated on the sides and at the top by agar gel (0.5% by weight agarose powder dissolved in water at 65° C. and solidified overnight in a 4° C. refrigerator). The sample-agar gel complex was then covered by a plastic wrap to isolate the sample from evaporative cooling and sublimation which interfere with a consistent and correct measurement. In this system, water evaporation or ice sublimation from the tissue was negligible (weight change <5%) during the measurement. Finally, all measurements were made within 48 hours after tissue host sacrifice to avoid significant changes in water content. The measured thermal conductivity at 41° C. and 51° C. are shown in Table 2 above.

Example 8: Specific Heat Capacity Measurements

A power compensation type differential scanning calorimeter (DSC) was used (Perkin Elmer Diamond DSC) to measure the specific heat of the tissue-laden scaffolds. The temperature and the heat flow scale of the DSC were calibrated using cyclohexane (transition temperature of 6.54° C. with a latent heat of 31.25 J·g$^{-1}$) and n-octadecane (transition temperature of 28.24° C. with a latent heat of 241.42 J·g$^{-1}$). Measurements were conducted using 10-15 mg samples in crimped aluminum pans. Each measurement consisted of a temperature scan from 37° C. to 52° C. performed at 5° C./min and were bracketed with a 1 min isothermal step before and after the scan. It should be noted that specific heat calculations for the current study are based on the enthalpic measurements during heating using the DSC. The calculated specific heat capacities at 21° C. and 35° C. are shown in Table 2 above. This temperature range is reasonable as it includes the expected destructive temperature range of 45 to 52° C., and the PCL comprising the scaffold melts beyond 56° C. Thus, in this protocol the latent heat of phase change for the PCL was not included in the $C_P$ calculation.

Example 9: Protein Denaturation Measurements

Tissue-laden PCL scaffolds were soaked for an hour in a 0.9% (w/v) solution of NaCl (Sigma-Aldrich) in $D_2O$ (Sigma-Aldrich) to replace water with deuterium oxide. This deuteration step increased the likelihood that the $H_2O$ scissoring band would not overlap with the Amide I absorption band of the tissue protein at wavenumbers ranging from 1700-1600 cm$^{-1}$. Deuteration may not interfere with the protein denaturation kinetics measurement and may be used as a marker to assess protein structure in solutions and tissues. Protein denaturation was measured using a Nicolet iS50 FTIR Spectrometer (Thermo Fisher Scientific). The Fourier transform infrared (FTIR) spectrometer was equipped with an MCT-A detector and a temperature controlled attenuated total reflection (ATR) stage (MVP-Pro, Harrick Scientific). The sample was heated at a rate of 2° C.·min$^{-1}$ to thermally denature proteins, and the change in absorbance of the sample in the wavenumber range 4000-900 cm$^{-1}$ was recorded as a function of temperature. Spectral data acquisition was carried out using Omnic software (Thermo Fisher Scientific). Protein denaturation analysis was performed as described previously. Briefly, the heat denaturation profiles were obtained from the sample by subtracting the spectra at room temperature (25° C.) from all subsequent higher temperature spectra, and the second derivatives of these spectra were calculated with a 13 point smoothing factor using MATLAB software (MathWorks). Thermal denaturation was assessed by monitoring the area of the absorption band from 1630-1610 cm$^{-1}$. This region contains the Amide I β-sheet peak, the area of which increases with increasing protein denaturation and thus can be used to quantify the degree of denaturation. The temperature dependent area values obtained were normalized between 25° C. and 90° C. to get the sigmoidal fractional denaturation (FD) curve. The following equation was used for the calculation of fractional denaturation:

$$FD(T) = \frac{\text{Area at } T - \text{Area at } 25° \text{ C.}}{\text{Area at } 90° \text{ C.} - \text{Area at } 25° \text{ C.}}$$

Here, FD(T) denotes fractional denaturation as a function of temperature, T, and Area refers to the Amide I β-sheet peak area (1630-1610 cm$^{-1}$).

Figure 7A:
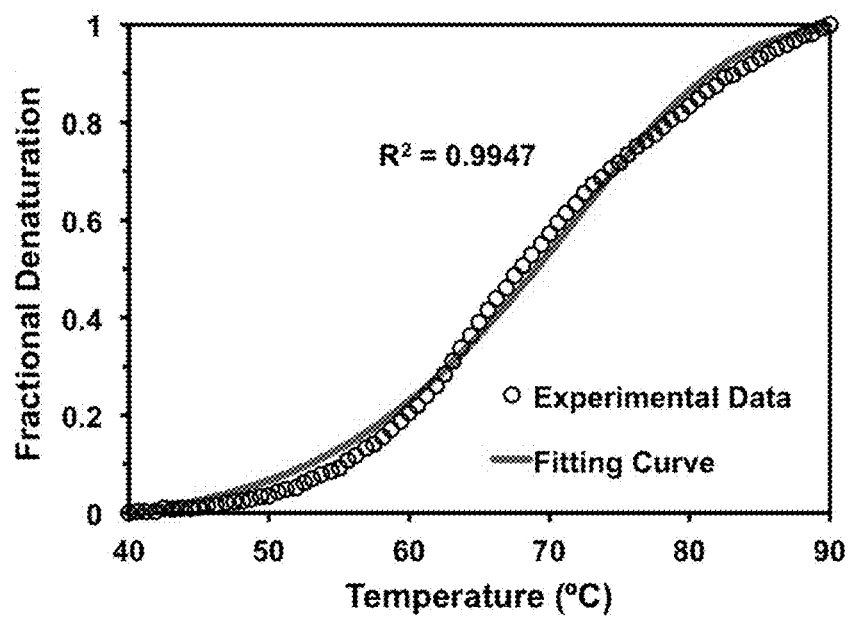
FIG. 7A illustrates a resulting fractional denaturation curve at various temperatures.
Figure 7B:
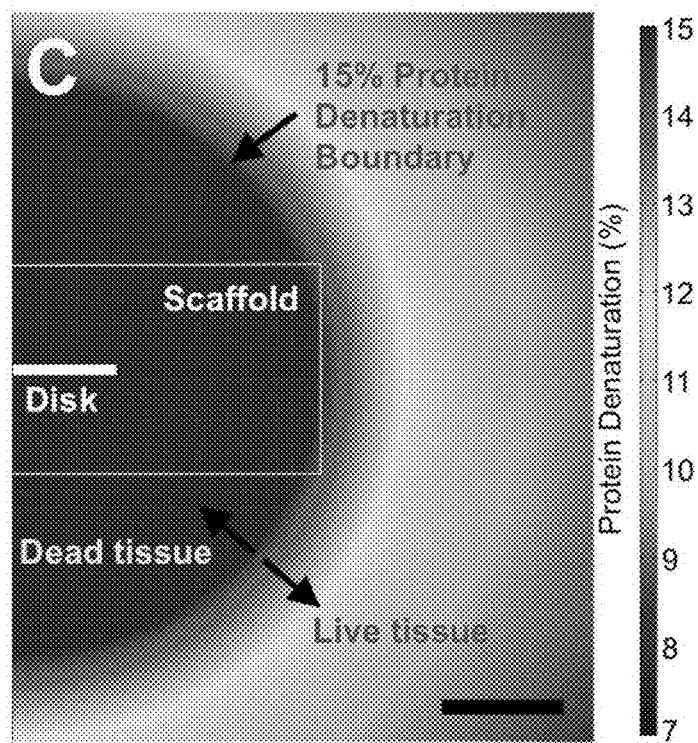
FIG. 7B illustrates a predicted cell damage profile in a tissue-laden composite scaffold.

FIG. 7A illustrates a resulting fractional denaturation curve at various temperatures. FIG. 7B illustrates a predicted cell damage profile in a tissue-laden composite scaffold. The 15% protein denaturation boundary may indicate an expected cell damage threshold.

Example 10: Inductive Heating Studies

For heating studies with bare metal disks, the disks were placed at the bottom of a 2 mL microcentrifuge tube with 1 mL of distilled water. A type T thermocouple (OMEGA Engineering) was placed on the metal disk to measure the surface temperature. This assembly was placed in the center of a 2.75-turn, water-cooled copper coil connected to a 1 kW Hotshot inductive heating system (Ameritherm) to generate the applied magnetic field. The coil current was adjusted to achieve different magnetic field strengths as previously described. Briefly, COMSOL version 3.5a was used to calculate the volume-averaged value of the field strength across the sample. The resonant frequency used for all studies was 360 kHz±10%. For ex vivo tissue-laden scaffold heating studies, harvested scaffolds were placed at the bottom of a 2 mL centrifuge tube with 1 mL of PBS. A type T thermocouple (OMEGA Engineering) was placed on the metal disk to measure the surface temperature. This assembly was placed in the center of the copper coil and an oscillating magnetic field was applied for 15 minutes. For ex vivo tissue-laden scaffold heating studies, harvested scaffolds were used for measuring temperature profiles and cell viability. For experimental temperature profiles needed for specific absorption rate (SAR) calculation, scaffolds were placed in a 1.5 mL microcentrifuge tube with 1 mL of ultrasound gel. A type T thermocouple was placed 1.20 mm (in vicinity of disk) and 1.85 mm (close to edge of scaffold) from the center of the scaffold to measure the temperature gradient within the tissue-laden composite scaffold, which was treated for 4 minutes at 15 kA·m$^{-1}$. For ex vivo viability studies, tissue-laden scaffolds were placed in 1 mL of phosphate-buffered saline (PBS) and treated for 10 minutes at 15 kA·m$^{-1}$.

For in vivo tissue-laden scaffold heating studies, due to size limitations of the animal body and coil dimensions, the implanted PCL-Al scaffold could not be placed in the center of the radiofrequency coil. To ensure a field strength of 15 kA·m$^{-1}$ at the scaffold location, the center of the radiofrequency coil was set to 20 kA·m$^{-1}$ and placed 9.25 mm above the implant site. FLIR E30 and FLIR A300 IR-cameras (FLIR Systems Inc.) were used to capture infrared (IR) images before and during 10-minute treatment. An in vivo heating profile was generated by analyzing the average temperature values in a ~5 mm diameter circular region encompassing the implanted scaffold in the IR video during treatment using ThermaCAM Researcher Professional 2.10 software (FLIR Systems Inc.). To evaluate the acute effect of treatment, scaffolds were harvested immediately after treatment to assess cellular viability. For chronic effects of thermal injury, mice were allowed to recover for three days, after which scaffolds were harvested and placed in formalin for histological analysis. Day three was chosen for this analysis in accordance with previous literature demonstrating that chronic effects of thermal therapy can be detected as early as three days after treatment.

Figure 8A:
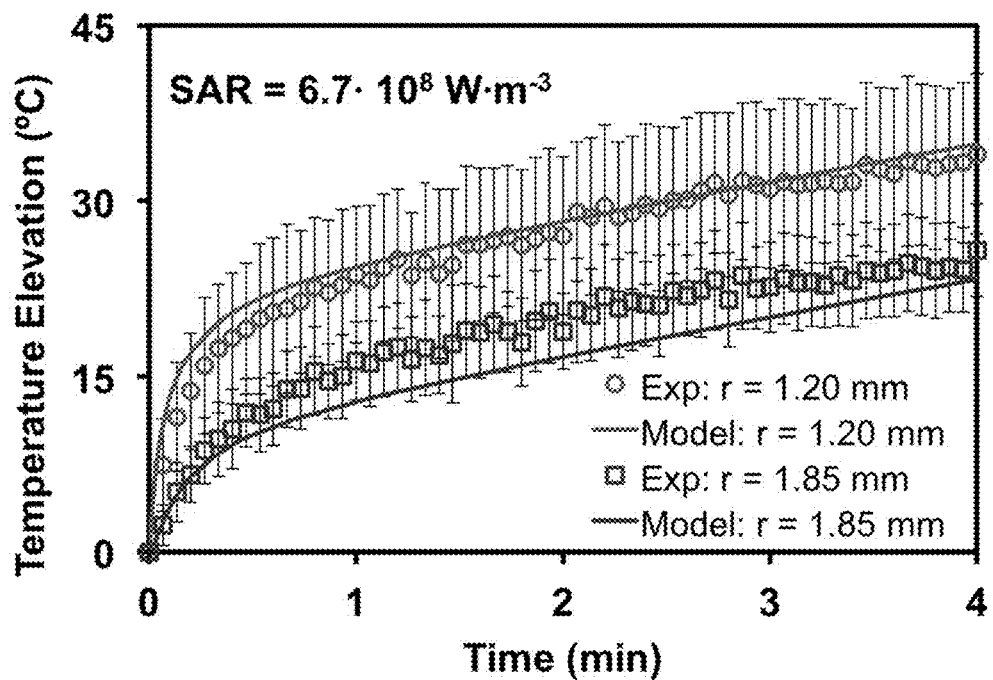
FIG. 8A illustrates temperature elevation of the tissue over time at 1.2 mm (top circles) and 1.85 mm (bottom circles) radially from the center of the disk at 15 kA·m-1 and 360 kHz.
Figure 8B:
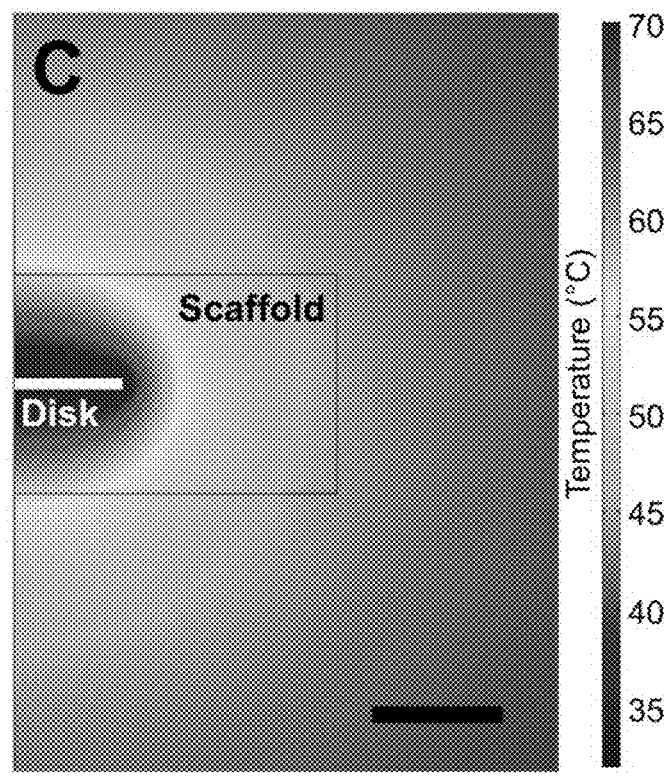
FIG. 8B illustrates a predicted temperature profile through the composite tissue-laden scaffold after 10 minutes of heating at 15 kA·m-1 and 360 kHz

FIG. 8A illustrates temperature elevation of the tissue over time at 1.2 mm (top circles) and 1.85 mm (bottom circles) radially from the center of the disk at 15 kA·m$^{-1}$ and 360 kHz. Solid lines illustrate model predictions at each location from optimized SAR (6.7×10$^8$ W·m$^{-3}$). FIG. 8B illustrates a predicted temperature profile through the composite tissue-laden scaffold after 10 minutes of heating at 15 kA·m$^{-1}$ and 360 kHz.

Example 11: Heat Transfer Modeling

The Multiphysics finite elements package (COMSOL 5.2a) was employed to perform finite element analysis on the temperature distribution. Electromagnetic field equations were solved in the frequency domain using the mef module in COMSOL 5.2a, while the heat equation was solved in time domain. For numerical stability, the time step size of the heat equation was set to 0.001 sec, and both the absolute and relative tolerance of the solver were set to 1E-6. To mimic our experimental design, one terminal of the 2.5 turn coil is set at I=250 A, and the other side of the coil is grounded. The heat transfer module (ht) is used to study the heat generated by the disk and the temperature gradient. The heat source is coupled to volumetric loss density from the electromagnetic module (mef).

For the tissue-laden scaffolds, the bioheat equation governs heat transfer in the tissue and can be used to determine the time-dependent temperature distribution T that may be caused by induced eddy currents:

$$\rho C_P \frac{\partial T}{\partial t} = k \nabla^2 T + SAR + \omega \rho_b C_b (37 - T) + Q_m$$

where $\rho$ is the density of the tissue [kg·m$^{-3}$], $C_P$ is the specific heat capacity [J·kg$^{-1}$·°C.$^{-1}$], k is the thermal conductivity [W·m$^{-1}$·°C.$^{-1}$], and SAR is the power density dissipated by the induced eddy currents in either the tissue or the ferromagnetic implant [W·m$^{-3}$]. The heat generated by metabolic processes and the heat exchange due to blood perfusion in soft biological tissues may be noted by SAR and $\omega \rho_b C_b (37-T)$ respectively.

Predicting optimal conditions for in vivo radiofrequency heating applications requires knowing spatial temperature profiles within the tissue-laden scaffold during treatment to model the resulting cellular damage. Various thermal properties of tissue-laden PCL scaffolds were evaluated to model expected temperature profiles, as shown in Table 2 above. Density, $\rho$, was found to be 1.06 g·mL$^{-1}$. Specific heat capacity, $C_P$, was measured using differential scanning calorimetry to be $C_P$ [J·g$^{-1}$·K$^{-1}$]=0.0232·T+2.5008, where T is in °C. The thermal conductivity, k, evaluated using a 3$\omega$ sensor, was k [W·m$^{-1}$·K$^{-1}$]=−0.0005·T+0.5077, where T is in °C.

The heat source Q is given by:

$$Q = \frac{1}{2}\sigma|E|^2$$

where $\sigma$ is the electrical conductivity [S·m$^{-1}$] and E is the electric field intensity [V·m$^{-1}$], governed by:

$$(j\omega\sigma - \omega^2\varepsilon)E + \nabla \times \left(\frac{1}{\mu}\nabla \times E\right) = -j\omega J$$

Here, $w$ is the angular frequency [rad·s$^{-1}$], $\varepsilon$ is the permittivity [F·m$^{-1}$], and $\mu$ is the permeability [N·A$^{-2}$], and J is the external current density [H·m$^{-1}$]. Multiphysics finite element package (COMSOL 5.2a) was used to perform finite element analysis on the temperature distribution T. Electromagnetic field equations were solved in the frequency domain, while the bioheat equation was solved in the time domain. For numerical stability, we set the time step size of the bioheat equation to 0.001 s, and both the absolute and the relative tolerance of the solver were set to 1×10$^{-6}$.

An important parameter in eddy current modeling is the skin depth, $\delta$ (Table 3). In some examples, the size of disks may not be larger than skin depth, as adding material once the disk is larger than the skin depth does not increase the heating, since the electrons cannot penetrate further than skin depth.

Rapid heating through an oscillating magnetic field can be achieved by inducing large eddy currents in a conducting material. Thus, we evaluated the ability of 100 μm-thick metal disks to heat in response to the presence of an oscillating magnetic field. Aluminum disks of various diameters, as seen in FIG. 5A, were submerged in water and placed in a radiofrequency coil, and an oscillating magnetic field at 15 kA·m$^{-1}$ at 360 kHz was applied. As the disk diameter increased from 1.13±0.05 mm to 1.90±0.04 mm, the temperature elevation achieved from the surface of the disk increased from 19±2° C. to 58±4° C., indicating a positive correlation between disk diameter and temperature elevation, as shown in FIG. 5B. With the disk diameter fixed at 1.70±0.04 mm, the temperature elevation could also be modulated at fixed frequency of 360 kHz by increasing the magnetic field strength from 5 kA·m$^{-1}$ to 20 kA·m$^{-1}$, resulting in temperature elevations of 4.8±0.9° C., 20.3±1.9° C., 47.1±2.6° C., and 56.2±4.4° C., respectively, as shown in FIG. 5C. The type of metal used also affected its response to the magnetic field, with 1.68±0.07 mm diameter copper disks generating a temperature elevation of 43±3° C., in comparison to 47±3° C. for 1.70±0.04 mm diameter aluminum disks, as shown in FIG. 5D. These results are consistent with previous work that shows power absorption of a conducting disk is based on radius, conductivity, and magnetic field strength.

The skin depth (δ) is given by the following equation:

$$\delta = \sqrt{\frac{2}{\pi \mu \sigma f}}$$

Where μ, σ and f are relative permeability, electrical conductivity, and coil frequency, respectively. Skin depth is an important design parameter as the current does not flow homogeneously through a conductor, but is confined near the surface. The skin depth is the distance from the surface which contains ~64% of the current and 80% of the power, and thus 99% of the current flows within a layer four times the skin depth from the surface. To achieve the improved heating potential, the radius of the disk may be at least 4 times the skin depth. Based on the skin depths of aluminum and copper, as shown in Table 3, the disk radii may be at least 548 μm and 436 μm for aluminum and copper, respectively, for an alternating field resonating at 360 kHz. Thus, the 1.70±0.04 mm aluminum disks were chosen for the remaining proof of concept studies, as they meet the thermal seed skin depth designs and are able to generate sufficient temperature elevations for rapid high-temperature thermal ablation.

TABLE 3

Skin depth for the two metals used in our studies at a frequency of 360 kHz.

| Material | Relative Permeability (μ) | Conductivity (σ) | Skin Depth (δ) |
|---|---|---|---|
| Copper | 0.999991 | 5.959 × 10$^7$ S/m | 108.6593 μm |
| Aluminum | 1.00002 | 3.766 × 10$^7$ S/m | 136.6723 μm |

Example 12: Calculating SAR

To extract the SAR induced by the metal disk, an inverse heat transfer analysis was performed by comparing the experimentally recorded temperature profile to a computational model. The model was built to mimic the experimental design with the known geometry, boundary and initial conditions, and electrical and thermal properties of the ultrasound gel, tissue-laden scaffold, and aluminum disk. We started with an initial guess for SAR in the model based on the theoretical SAR in a cylindrical metal. An objective function based on the least square residual fit was defined by the following expression:

$$LSQ = \frac{\sqrt{\sum_{i=1}^{M}[\varphi_i - T_i]^2}}{M}$$

where M is the total number of the measured temperature locations, and $\varphi_i$ and $T_i$ represent the experimentally measured and theoretically predicted temperatures, respectively, at those locations during the heating time. To solve for $T_i$, the bioheat equation, the above equation was solved in the time domain in COMSOL using the initial guess for SAR. The SAR value was then adjusted until the objective function reached its minimum, and the resulting value of SAR was used in all further modeling of predicted temperature profiles in the tissue-laden composite scaffold. Numerical stability and convergence were ensured by performing mesh reduction and discretization until no further changes were found upon refinement.

Example 13: Tissue Damage Modeling

Thermal tissue damage was modeled as a first order irreversible rate process as described in the literature. Protein denaturation was used as an indicator for tissue death. The kinetics for the protein denaturation process were evaluated from the protein fractional denaturation curve from the FTIR measurements using an Arrhenius type rate constant for the first order reaction process as described by the equations below:

$$FD(T) = 1 - \exp\left(-\frac{1}{B}\int_{T_0}^{T} k dT\right)$$

$$k = A\exp\left(-\frac{E_a}{RT}\right)$$

where FD(T) is the fractional denaturation of protein (measured by FTIR) at temperature T (K), B is the heating rate (K·s$^{-1}$), and k is the rate constant for the first order process (K·s$^{-1}$). $E_a$ and A are the activation energy (kJ·mol$^{-1}$) and the pre-exponential factor (s$^{-1}$) for the Arrhenius type rate constant, respectively. R is the universal gas constant (kJ·mol$^{-1}$·K$^{-1}$). The experimental data was used in the correlated parameter fit method described in to determine a numerical value for the constants A and Ea. These values were used in conjunction with the temperature profile obtained from COMSOL simulation to calculate the fractional denaturation of protein in and around the scaffold ex vivo. The spatial distribution of denatured protein was then used for prediction of cell death in the scaffold.

TABLE 4

Thermal damage properties of tissue-laden scaffolds.

| Property | Value |
| --- | --- |
| $E_a$ (kJ · mol$^{-1}$) | 89.1 |
| A (s$^{-1}$) | $1.187 \times 10^{11}$ |

Example 14: Viability Assays

Viability of cells in tissue-laden scaffolds was determined by treating the cells with cell viability reagent WST-1 (Takara Bio). Scaffolds were transferred to 500 µL of fresh media (DMEM containing 10% fetal bovine serum, 1% L-glutamine, and 1% penicillin-streptomycin; Thermo Fisher Scientific). Microscissors were used to mince the scaffolds into small pieces. 50 µL of WST-1 reagent was added to each sample and incubated at 37° C. for 2 hours. Media samples were used as a negative control for background measurement, and 70% ethanol treatment of tissue-laden scaffolds was performed as a control for total cell death. For ethanol treatment, tissue-laden scaffolds were minced in 500 µL of 70% ethanol and incubated on ice for 1 hour. Following ethanol incubation, the samples were centrifuged at 14,000×g for 5 minutes, and the supernatant was replaced with 500 µL of fresh media prior to addition of the WST-1 reagent. After WST-1 treatment, all samples were vortexed and centrifuged at 14,000×g for 5 min. Duplicates of 200 µL per sample were transferred to a 96-well plate. Media samples were used as a negative control for background measurement. Absorbance of each well was measured at a wavelength of 440 nm with a Synergy H1 microplate reader (BioTek Instruments).

PCL-Al scaffolds with tissue exhibited a 26° C. temperature rise when placed in an oscillating magnetic field with a strength of 15 kA/m and a frequency of 360 kHz. The amount of power generated by aluminum disks at these magnetic field conditions was $6.7 \times 10^8$ W/m$^3$. This temperature increase was sufficient to reduce cell viability by 100% in PCL-Al composite scaffolds compared to non-heated PCL-Al scaffolds. Hematoxylin and eosin staining revealed significant changes to tissue morphology immediately after removal from the magnetic field in metal composite scaffolds, compared to non-heated PCL-Al scaffolds. This approach could may also be applied in vivo by placing a mouse directly in the radiofrequency coil.

FIG. 9A illustrates a viability assay of cells in tissue-laden scaffolds with and without ex vivo treatment (10 minutes at 15 kA·m$^{-1}$ and 360 kHz). Black dashed lines indicate a background signal from no scaffold control. FIGS. 9B and 9C illustrate sections of tissue-laden PCL (FIG. 9B) and PCL-Al (FIG. 9C) scaffolds following ex vivo treatment.

Figure 10A:
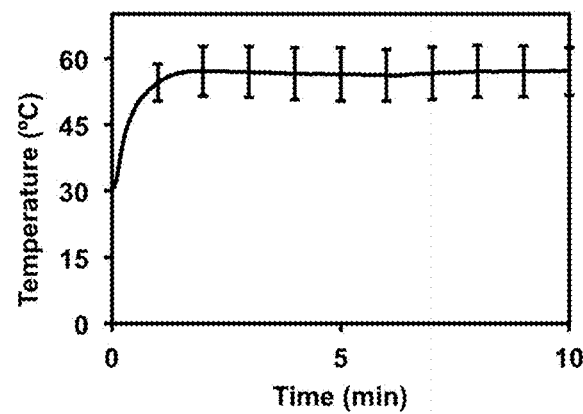
FIG. 10A illustrates temperatures of a PCL-Al scaffold as a function of time during treatment.
Figure 10B:
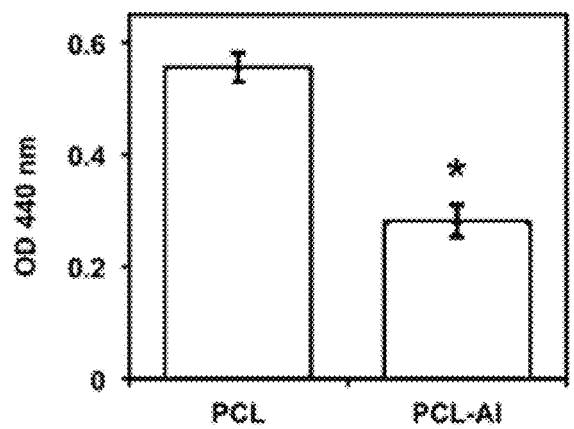
FIG. 10B illustrates a viability assay of treated PCL-Al and PCL immediately after treatment.
Figure 10C:
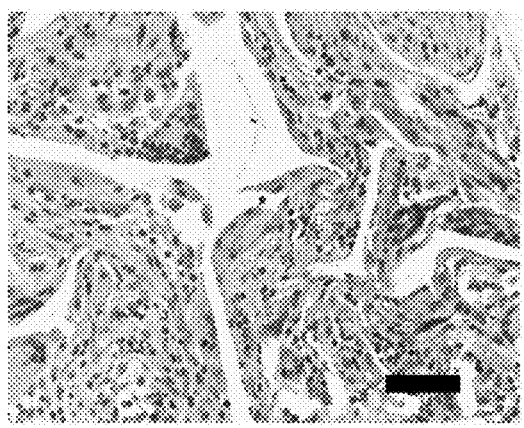
FIG. 10C illustrates a section of a tissue-laden PCL scaffold three days post-treatment.
Figure 10D:
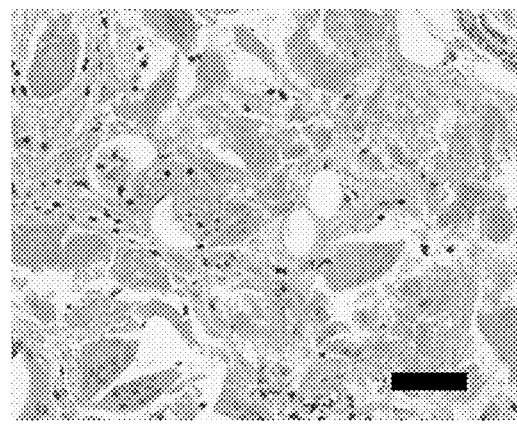
FIG. 10D illustrates a section of a tissue-laden composite PCL-AL scaffold three days post-treatment.

FIG. 10A illustrates temperatures of a PCL-Al scaffold as a function of time during treatment. FIG. 10B illustrates a viability assay of treated PCL-Al and PCL immediately after treatment. FIGS. 10C and 10D are sections of tissue-laden PCL and composite PCL-AL scaffolds three days post-treatment.

Recruitment of tumor cells to the scaffold may be mediated by immune cells, and after thermal therapy the site may undergo a wound healing process that may create an inflammatory environment that may facilitate future recruitment of tumor cells. In addition, the immune cells present in the scaffold provide an opportunity to combine the focal therapy with immunotherapy using the tumor-specific antigens released following hyperthermia.

Figure 11A:
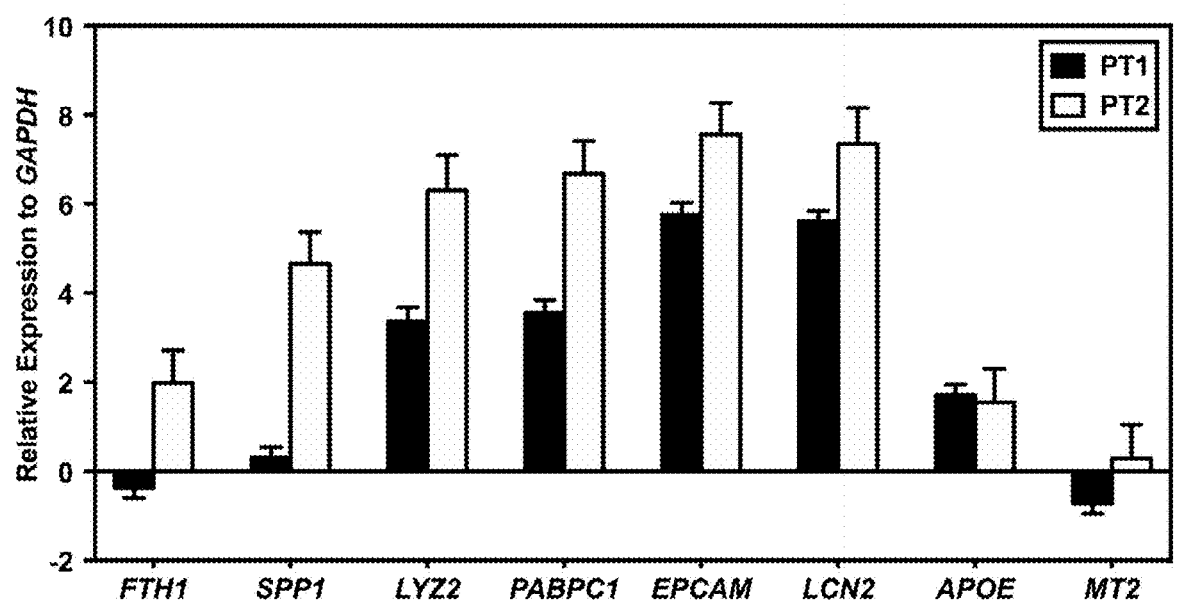
FIG. 11A is a graph of qRTPCR analysis of 4T1 primary tumors, PT1 and PT2, to identify highly expressed genes.
Figure 11B:
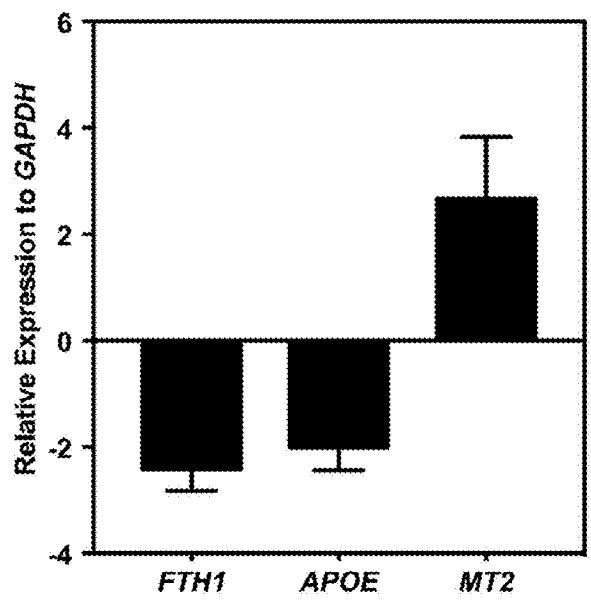
FIG. 11B is a graph of gene expression analysis of PCL scaffolds from tumor-free mice.
Figure 11C:
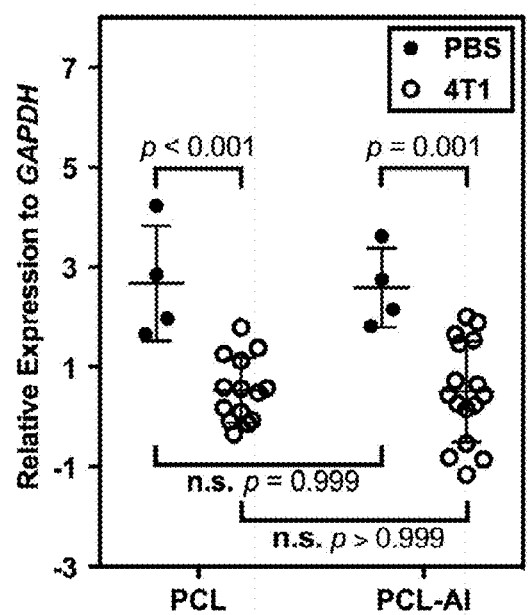
FIG. 11C is a chart of a comparison of MT2 relative expression in PCL and PCL-Al scaffolds from mice with either PBS only or 4T1 inoculations.

PCL-Al scaffolds were evaluated to verify that the ability to recruit metastatic breast cancer cells was not affected by the presence of the metal disk. FIGS. 11A-11C illustrate in vivo capture of metastatic cancer cells to composite scaffolds. To evaluate cancer cell recruitment to the scaffolds, a qRT-PCR approach developed for identifying melanoma cells was modified to identify and evaluate genes highly expressed in 4T1 tumors. Eight genes (FTH1, SPP1, LYZ2, PABPC1, EPCAM, LCN2, APOE, and MT2) were selected as potentially highly expressed based on previously published microarray data (GSE64193) of harvested 4T1 tumors. FIG. 11A is a graph of qRT-PCR analysis of 4T1 primary tumors, PT1 and PT2, to identify highly expressed genes. Relative expression (CtGENE−CtGAPDH) is mean±SD, n=2. Further qRT-PCR analysis revealed that three of these genes, FTH1, APOE, and MT2, were consistently highly expressed, as evidenced by low relative expression to the GAPDH reference gene, in two 4T1 primary tumors from our mouse model (Fig. S3A). FIG. 11B is a graph of gene expression analysis of PCL scaffolds from tumor-free mice. Relative expression (CtGENE−CtGAPDH) is mean±SD, n=4. MT2 was selected to evaluate the presence of metastatic cells within the implanted scaffolds, as of the three genes highly expressed in 4T1 tumors, MT2 exhibited the lowest expression in subcutaneous scaffolds from tumor-free mice (Fig. S3B). Both PCL and PCL-Al scaffolds exhibited statistically higher expression of MT2 compared to their respective control scaffolds from tumor-free mice, which indicates the presence of metastatic cells. Additionally, there was no significant difference in MT2 expression between PCL and PCL-Al scaffolds in tumor-bearing mice (Fig. S3C). FIG. 11C is a chart of a comparison of MT2 relative expression in PCL and PCL-Al scaffolds from mice with either PBS only or 4T1 inoculations. Relative expression (CtGENE−CtGAPDH) is mean±SD, n≥4. These results demonstrate that the ability of PCL scaffolds to recruit 4T1 tumor cells is unaffected by the addition of a metal disk to form the composite PCL-Al scaffold.

Various examples have been described. These and other examples are within the scope of the following claims.

What is claimed is:

1. A method, comprising:
    applying, by an electromagnetic source, an electromagnetic induction stimulus to an implantable device implanted in a body of a patient at a target strength and target frequency for a target duration,
    wherein the implantable device comprises:
        an electrically conductive or electrically semiconductive material comprising a plurality of particles; and
        a biocompatible porous scaffold around the electrically conductive or electrically semiconductive material,
    wherein the biocompatible porous scaffold comprises a biocompatible polymer and pores configured to capture metastatic cells,
    wherein the plurality of particles is disposed in the biocompatible polymer substantially throughout a volume of the biocompatible porous scaffold, and
    wherein the electromagnetic induction stimulus is selected to cause the electrically conductive or electrically semiconductive material to heat at least a portion of the biocompatible porous scaffold to at least a target temperature.

2. The method of claim 1, further comprising selecting the target strength, the target frequency, the target duration, and the target time to cause the electrically conductive or electrically semiconductive material to resistively heat the metastatic cells to kill at least 85% of metastatic cells in the biocompatible porous scaffold.

3. The method of claim 1, wherein the target temperature is between 40 degrees Celsius and 50 degrees Celsius, the target duration is between about one minute and about ten minutes, the target strength is between about 10 kA/m and about 100 kA/m, and the target frequency is between about 100 kHz and about 500 kHz.

4. The method of claim 1, wherein the electromagnetic induction stimulus is selected to cause the electrically conductive or electrically semiconductive material to heat substantially all of the biocompatible porous scaffold to at least the target temperature.

5. The method of claim 1, wherein the target temperature is selected to kill metastatic cells up to about 2 mm from a surface of the electrically conductive or electrically semiconductive material.

6. The method of claim 1, further comprising selecting the target strength, the target frequency, the target duration, and the target time to cause the electrically conductive or electrically semiconductive material to resistively heat the metastatic cells to kill substantially all metastatic cells in the biocompatible porous scaffold.

7. The method of claim 1, wherein the electromagnetic induction stimulus is selected to cause the electrically conductive or electrically semiconductive material to cause at least about 15% protein denaturation around the device.

8. The method of claim 1, wherein the electromagnetic induction stimulus is selected to cause the electrically conductive or electrically semiconductive material to create a specific absorption rate of at least about $3\times10^8$ W/m$^3$.

9. A device, comprising:
an implantable device, comprising:
an electrically conductive or electrically semiconductive material comprising a plurality of particles; and
a biocompatible porous scaffold around the electrically conductive or electrically semiconductive material; and
an electromagnetic source configured to apply an electromagnetic induction stimulus to the implantable device at a target strength and target frequency for a target duration,
wherein the biocompatible porous scaffold comprises a biocompatible polymer and pores configured to capture metastatic cells,
wherein the plurality of particles is disposed in the biocompatible polymer substantially throughout a volume of the biocompatible porous scaffold, and
wherein the electromagnetic induction stimulus is configured to cause the electrically conductive or electrically semiconductive material to heat at least a portion of the biocompatible porous scaffold to at least a target temperature.

10. The device of claim 9,
wherein the pores have a size between about 100 μm and about 500 μm, and
wherein the plurality of particles is disposed in the biocompatible polymer and distributed substantially evenly throughout a volume of the biocompatible porous scaffold.

11. The device of claim 9, wherein the plurality of particles has an average diameter between about 50 μm and about 200 μm.

12. The device of claim 9, further comprising a biocompatible coating between the electrically conductive or electrically semiconductive material and the biocompatible porous scaffold.

13. The device of claim 12, wherein the biocompatible coating defines a thickness between about 1 μm and about 50 μm.

14. The method of claim 1, further comprising implanting the implantable device in the body of the patient.

* * * * *